(12) United States Patent
LeBoeuf, II et al.

(10) Patent No.: US 12,044,552 B2
(45) Date of Patent: *Jul. 23, 2024

(54) METAL DETECTOR FOR DETECTING INSERTION OF A SURGICAL DEVICE INTO A HOLLOW TUBE

(71) Applicant: GLOBUS MEDICAL, INC., Audubon, PA (US)

(72) Inventors: Robert J. LeBoeuf, II, Salem, NH (US); James Yau, Methuen, MA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/308,281

(22) Filed: Apr. 27, 2023

(65) Prior Publication Data

US 2023/0258475 A1 Aug. 17, 2023

Related U.S. Application Data

(63) Continuation of application No. 17/095,143, filed on Nov. 11, 2020, now Pat. No. 11,668,588, which is a
(Continued)

(51) Int. Cl.
*A61B 34/20* (2016.01)
*A61B 6/03* (2006.01)
(Continued)

(52) U.S. Cl.
CPC ............... *G01D 5/20* (2013.01); *A61B 6/032* (2013.01); *A61B 17/1703* (2013.01); *A61B 34/20* (2016.02); *A61B 34/70* (2016.02); *A61B 2034/2051* (2016.02); *A61B 2034/2055* (2016.02); *A61B 2034/2057* (2016.02);
(Continued)

(58) Field of Classification Search
CPC ........ A61B 17/1703; A61B 2034/2051; A61B 2034/2055; A61B 2034/2057; A61B 2034/2065; A61B 2034/301; A61B 2034/305; A61B 2090/062; A61B 2090/0804; A61B 2090/376;
(Continued)

(56) References Cited

U.S. PATENT DOCUMENTS 4,150,293 A 4/1979 Franke
5,246,010 A 9/1993 Gazzara et al.
(Continued)

FOREIGN PATENT DOCUMENTS

JP H03252191 A 11/1991
JP 2012021970 A 2/2012

OTHER PUBLICATIONS

US 8,231,638 B2, 07/2012, Swarup et al. (withdrawn)

*Primary Examiner* — Christopher L Cook

(57) ABSTRACT

Apparatus, systems, and methods for detecting the presence of a metallic surgical instrument. A metal detector for detecting insertion of a metallic surgical device into a hollow tube may include a switch, resonant circuit and a controller. The resonant circuit has a capacitor and a coil mounted to the hollow tube. The controller turn on the switch for a preselected time to temporarily provide a current to the resonant circuit and analyzes a resulting decaying voltage waveform originating from the resonant circuit when the switch is turned off in order to determine the presence and longitudinal depth of the metallic surgical device in the hollow tube.

20 Claims, 19 Drawing Sheets

Related U.S. Application Data continuation of application No. 15/068,845, filed on Mar. 14, 2016, now Pat. No. 10,866,119.

(51) Int. Cl.
- *A61B 17/17* (2006.01)
- *A61B 34/00* (2016.01)
- *G01D 5/20* (2006.01)
- A61B 34/30 (2016.01)
- A61B 90/00 (2016.01)

(52) U.S. Cl.
CPC ....... *A61B 2034/2065* (2016.02); *A61B 34/30* (2016.02); *A61B 2034/301* (2016.02); *A61B 2034/305* (2016.02); *A61B 2090/062* (2016.02); *A61B 2090/0804* (2016.02); *A61B 2090/376* (2016.02); *A61B 2090/3966* (2016.02)

(58) Field of Classification Search
CPC . A61B 2090/3966; A61B 34/20; A61B 34/30; A61B 34/70; A61B 6/032; G01D 5/20
See application file for complete search history.

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |

(56) References Cited

U.S. PATENT DOCUMENTS

| | | |
|---|---|---|
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Trembley et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jenser |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |

(56) References Cited

U.S. PATENT DOCUMENTS

| | | |
|---|---|---|
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |

(56) References Cited

U.S. PATENT DOCUMENTS

| | | |
|---|---|---|
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |

(56) References Cited

U.S. PATENT DOCUMENTS

| | | |
|---|---|---|
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275955 A1 | 9/2014 | Crawford et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

METAL DETECTOR FOR DETECTING INSERTION OF A SURGICAL DEVICE INTO A HOLLOW TUBE

CROSS-REFERENCE TO RELATED APPLICATION(S)

This application is a continuation of U.S. patent application Ser. No. 17/095,143 filed on Nov. 11, 2020, which is a continuation of U.S. Ser. No. 15/068,845 filed on Mar. 14, 2016 (published as U.S. Pat. Pub. No. 2017-0261348), which is hereby incorporated by reference in its entirety for all purposes.

TECHNICAL FIELD

The present invention relates to metal detectors, systems, and methods, and in particular, metal detectors for detecting a metallic surgical instrument.

BACKGROUND OF THE INVENTION

Conventional metal detectors use a power-consuming resonance circuit which is always turned on, and detects the change in electromagnetic properties, e.g., a Q value, of an inductor in the resonance circuit. When a piece of metal is near the resonance circuit, the metal detector will detect the change in Q-value to determine whether a metal has been found.

One problem with such a conventional metal detector is that because the resonant circuit is always on, the detector can waste a substantial amount of power. In the context of performing medical procedures using a portable robot, it is important to use as little power as possible. Therefore, there is a need to provide a device and method for more efficiently detecting the presence of metal.

SUMMARY

According to one aspect of the present invention, a metal detector for detecting insertion of a metallic surgical device into a hollow tube is provided. The metal detector includes a switch, resonant circuit and a controller. The resonant circuit includes a capacitor and a coil connected to the capacitor in parallel. The coil is mounted to the hollow tube. The controller is adapted to turn on the switch for a preselected time to temporarily provide a current to the resonant circuit and analyzes a resulting decaying voltage waveform originating from the resonant circuit when the switch is turned off in order to determine the presence of the metallic surgical device in the hollow tube.

According to another aspect of the present invention, a method of detecting insertion of a metallic surgical device into a hollow tube is provided. Initially, a power supply is connected to a resonant circuit having a capacitor and an inductor mounted to the hollow tube. After a preselected time period, the power supply is disconnected from the resonant circuit. Once the power supply is disconnected, the resonant circuit generates a decaying waveform. The decaying waveform has a different shape depending on whether a metallic surgical device has been inserted into the hollow tube or not. The presence of the metallic surgical device in the hollow tube is then determined based on the generated decaying waveform.

By providing current to the resonant circuit for only a short period of time, the present invention advantageously saves power. Moreover, the ability to adjust the switch-on period allows for various pre-charge levels of the inductor, or the volt-second product, or the flux.

DETAILED DESCRIPTION OF THE INVENTION

Briefly, the metal detection system of the present invention switches on a resonant circuit for a very short period of time to provide current to the inductor positioned around the hollow tube and then analyzes the resulting decaying waveform once the current to the inductor is shut off. The naturally oscillating decaying waveform can be analyzed to detect whether a metal object is inside the hollow tube. Moreover, the decaying waveform can also be used to determine the depth of insertion of the metal object inside the hollow tube.

The present technique has several advantages over conventional methods. First, very little energy is required since a small initial energy is required to obtain a relatively high signal-to-noise ratio (SNR) and inductance sensitivity. Second, the initial energy is easily adjusted by adjusting the on-time of the switch SW1. This sets the initial flux in the inductor L, which in turn, allows for variable sensitivities. This can dynamically change any required inductive sensitivity, should the resonant circuit be in an electrically harsh environment. The frequency of the excitation, or ringing of the coil, may also dynamically be adjusted so that more samples can be taken. These values can then be averaged to obtain better SNR.

FIGS. 1-14 describe robotic systems that can incorporate the present metal detector which will be described with reference to FIGS. 15-22.

Figure 1:
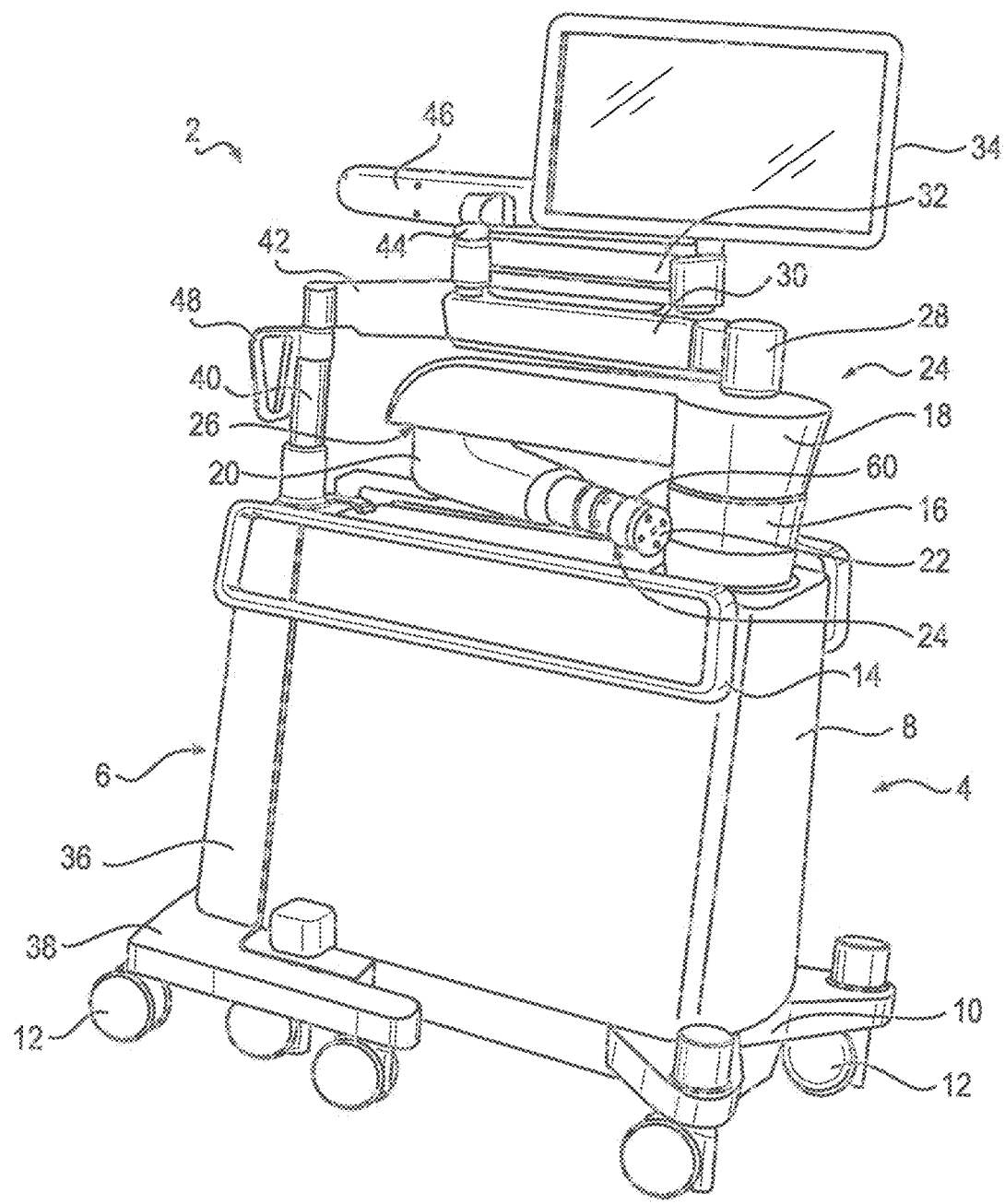
FIG. 1 illustrates an embodiment of an automated medical system.

FIG. 1 illustrates an embodiment of an automated medical system 2. Prior to performance of an invasive medical procedure, a three-dimensional ("3D") image scan may be taken of a desired surgical area of a patient and sent to a computer platform in communication with an automated medical system 2. In some embodiments, a physician may then program a desired point of insertion and trajectory for a surgical instrument to reach a desired anatomical target within or upon the body of the patient. In some embodiments, the desired point of insertion and trajectory may be planned on the 3D image scan, which in some embodiments, may be displayed on a display. In some embodiments, a physician may plan the trajectory and desired insertion point (if any) on a computed tomography scan (hereinafter referred to as "CT scan") of the patient. In some embodiments, the CT scan may be an isocentric C-arm type scan, or any other similar type scan, or intraoperative CT scan as is known in the art. However, in some embodiments, any known 3D image scan may be used in accordance with the embodiments of automated medical system 2.

A medical procedure may begin with automated medical system 2 moving from medical storage to a medical procedure room. Automated medical system 2 may be maneuvered through doorways, halls, and elevators to reach a medical procedure room. Within the room, automated medical system 2 may be physically separated into two separate and distinct systems, a robot support system 4 and a camera tracking system 6. Robot support system 4 may be positioned adjacent the patient at any suitable location to properly assist medical personnel. Camera tracking system 6 may be positioned at the base of the patient or any other location suitable to track movement of robot support system 4 and the patient. Robot support system 4 and camera tracking system 6 may be powered by an onboard power source and/or plugged into an external wall outlet.

Automated medical system 2, as illustrated in FIG. 1, may assist surgeons and doctors during medical procedures. Automated medical system 2 may assist surgeons and doctors by holding tools, aligning tools, using tools, guiding tools, and/or positioning tools for use. In embodiments, as illustrated in FIG. 1, automated medical system 2 may comprise of a robot support system 4 and a camera tracking system 6. Both systems may be coupled together by any suitable means. Suitable means may be, but are not limited to mechanical latches, ties, clamps, buttresses, magnetic and/or magnetic surfaces. The ability to combine robot support system 4 and camera tracking system 6 may allow for automated medical system 2 to maneuver and move as a single unit. This combination may allow automated medical system 2 to have a small footprint in an area, allow easier movement through narrow passages and around turns, and allow and storage within a smaller area.

Robot support system 4 may be used to assist a surgeon by orienting, positioning, holding and/or using tools during a medical procedure. To properly utilize, position, and/or hold tools, robot support system 4 may rely on a plurality of motors, computers, and/or actuators to function properly. Illustrated in FIG. 1, robot body 8 may act as the structure in which the plurality of motors, computers, and/or actuators may be secured within robot support system 4. Robot body 8 may also provide support for robot telescoping support arm 16. In embodiments, robot body 8 may be made of any suitable material. Suitable material may be, but is not limited to, metal such as titanium, aluminum, or stainless steel, carbon fiber, fiberglass, or heavy-duty plastic. The size of robot body 8 may provide a solid platform on which other components may connect and operate. Robot body 8 may house, conceal, and protect the plurality of motors, computers, and/or actuators that may operate attached components.

Robot base 10 may act as a lower support for robot support system 4. In embodiments, robot base 10 may support robot body 8 and may attach robot body 8 to a plurality of powered wheels 12. This attachment to the wheels may allow robot body 8 to move in space efficiently. Robot base 10 may run the length and width of robot body 8. Robot base 10 may be about an two inches to about ten inches tall. Robot base 10 may be made of any suitable material. Suitable material may be, but is not limited to, metal such as titanium, aluminum, or stainless steel, carbon fiber, fiberglass, or heavy-duty plastic or resin. Robot base 10 may cover, protect, and support powered wheels 12.

In embodiments, as illustrated in FIG. 1, at least one powered wheel 12 may be attached to robot base 10. Powered wheels 12 may attach to robot base 10 at any location. Each individual powered wheel 12 may rotate about a vertical axis in any direction. A motor may be disposed above, within, or adjacent to powered wheel 12. This motor may allow for automated medical system 2 to maneuver into any location and stabilize and/or level automated medical system 2. A rod, located within or adjacent to powered wheel 12, may be pressed into a surface by the motor. The rod, not pictured, may be made of any suitable metal to lift automated medical system 2. Suitable metal may be, but is not limited to, stainless steel, aluminum, or titanium. Additionally, the rod may comprise at the contact surface-side end a buffer, not pictured, which may prevent the rod from slipping and/or create a suitable contact surface. The material may be any suitable material to act as a buffer. Suitable material may be, but is not limited to, a plastic, neoprene, rubber, or textured metal. The rod may lift powered wheel 10, which may lift automated medical system 2, to any height required to level or otherwise fix the orientation of the automated medical system 2 in relation to a patient. The weight of automated medial system 2, supported through small contact areas by the rod on each wheel, prevents automated medical system 2 from moving during a medical procedure. This rigid positioning may prevent objects and/or people from moving automated medical system 2 by accident.

Moving automated medical system 2 may be facilitated using robot railing 14. Robot railing 14 provides a person with the ability to move automated medical system 2 without grasping robot body 8. As illustrated in FIG. 1, robot railing 14 may run the length of robot body 8, shorter than robot body 8, and/or may run longer the length of robot body 8. Robot railing 14 may be made of any suitable material, but is not limited to, metal such as titanium, aluminum, or stainless steel, carbon fiber, fiberglass, or heavy-duty plastic. Robot railing 14 may further provide protection to robot body 8, preventing objects and or personnel from touching, hitting, or bumping into robot body 8.

Robot body 8 may provide support for a Selective Compliance Articulated Robot Arm, hereafter referred to as a "SCARA." A SCARA 24 may be beneficial to use within the automated medical system due to the repeatability and compactness of the robotic arm. The compactness of a SCARA may provide additional space within a medical procedure, which may allow medical professionals to perform medical procedures free of excess clutter and confining areas. SCARA 24 may comprise robot telescoping support 16, robot support arm 18, and/or robot arm 20. Robot telescoping support 16 may be disposed along robot body 8. As illustrated in FIG. 1, robot telescoping support 16 may provide support for the SCARA 24 and display 34. In embodiments, robot telescoping support 16 may extend and contract in a vertical direction. Robot telescoping support 16 may be made of any suitable material, but not limited to, metal such as titanium or stainless steel, carbon fiber, fiberglass, or heavy-duty plastic. The body of robot telescoping support 16 may be any width and/or height in which to support the stress and weight placed upon it. In embodiments, medical personnel may move SCARA 24 through a command submitted by the medical personnel. The command may originate from input received on display 34 and/or a tablet. The command may come from the depression of a switch and/or the depression of a plurality of switches. Best illustrated in FIGS. 4 and 5, an activation assembly 60 may comprise a switch and/or a plurality of switches. The activation assembly 60 may be operable to transmit a move command to the SCARA 24 allowing an operator to manually manipulate the SCARA 24. When the switch, or plurality of switches, is depressed the medical personnel may have the ability to move SCARA 24 easily. Additionally, when the SCARA 24 is not receiving a command to move, the SCARA 24 may lock in place to prevent accidental movement by personnel and/or other objects. By locking in place, the SCARA 24 provides a solid platform upon which an end effector 22 and end effector tool 26 may be used during a medical operation.

Robot support arm 18 may be disposed on robot telescoping support 16 by any suitable means. Suitable means may be, but is not limited to, nuts and bolts, ball and socket fitting, press fitting, weld, adhesion, screws, rivets, clamps, latches and/or any combination thereof. In embodiments, best seen in FIGS. 1 and 2, robot support arm 18 may rotate in any direction in regard to robot telescoping support 16. Robot support arm 18 may rotate three hundred and sixty degrees around robot telescoping support 16. Robot arm 20 may connect to robot support arm 18 at any suitable location. Robot arm 20 may attach to robot support arm 16 by any suitable means. Suitable means may be, but is not limited to, nuts and bolts, ball and socket fitting, press fitting, weld, adhesion, screws, rivets, clamps, latches and/or any combination thereof. Robot arm 20 may rotate in any direction in regards to robot support arm 18, in embodiments, robot arm 20 may rotate three hundred and sixty degrees in regards to robot support arm 18. This may allow an operator to position robot arm 20 as desired.

Figure 4:
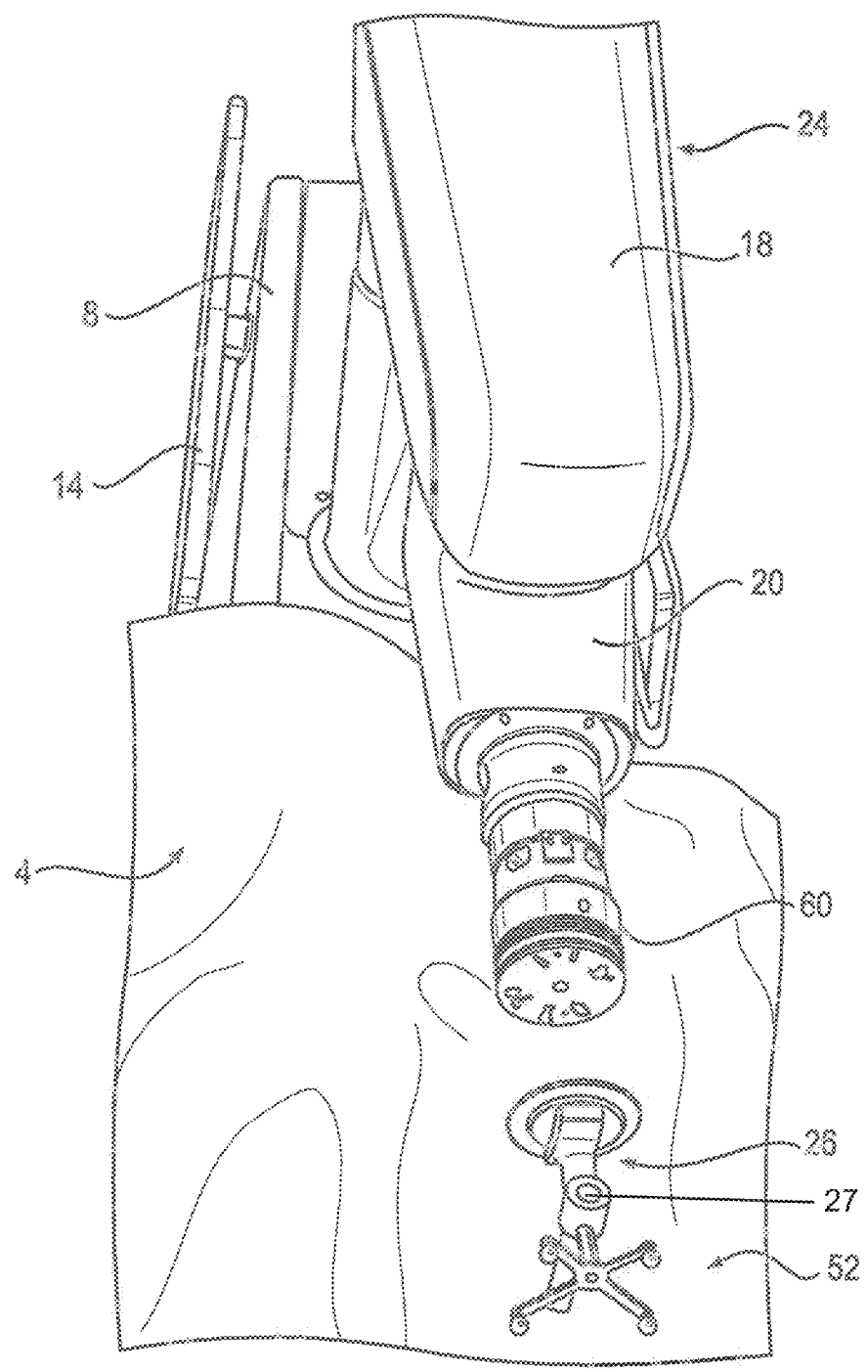
FIG. 4 illustrates an embodiment of a SCARA with end effector.

End effector 22 may attach to robot arm 20 in any suitable location. End effector 22 may attach to robot arm 20 by any suitable means. Suitable means may be, but is not limited to, latch, clamp, nuts and bolts, ball and socket fitting, press fitting, weld, screws, and/or any combination thereof. End effector 22 may move in any direction in relation to robot arm 20. This may allow a user to move end effector 22 to a desired area. An end effector tool 26, as illustrated in FIG. 4 may attach to end effector 22. End effector tool 26 may be any tool selected for a medical procedure. In some embodiments, the end effector tool 26 includes a tube portion have a hollow tube 27 extending therethrough. The hollow tube 27 is sized and configured to receive at least a portion of a surgical instrument. The hollow tube 27 is configured to be oriented by the robot arm 20 such that insertion and trajectory for the surgical instrument is able to reach a desired anatomical target within or upon the body of the patient. The surgical instrument may include at least a portion of a generally cylindrical instrument. By way of example, the surgical instrument may include one or more of a guide wire, cannula, a retractor, a drill, a reamer, a screw driver, an insertion tool, a removal tool, or the like. Although the hollow tube 27 is generally shown as having a cylindrical configuration, it will be appreciated by those of skill in the art that the hollow tube 27 may have any suitable shape, size and configuration desired to accommodate the surgical instrument and access the surgical site. End effector tool 26 may be disposed and removed from end effector 22. In embodiments, end effector tool 26 may have a dynamic reference array 52. Dynamic reference arrays 52, herein referred to as "DRAs", are rigid bodies which may be disposed on a patient and/or tool in a navigated surgical procedure. Their purpose may be to allow 3D localization systems to track the positions of tracking markers that are embedded in the DRA 52, and thereby track the real-time position of relevant anatomy. Radio-opaque markers may be seen, recorded, and/or processed by camera 46. This tracking of 3D coordinates of tracking markers may allow automated medical system 2 to find the DRA 52 in any space in relation to a patient 50.

As illustrated in FIG. 1, a light indicator 28 may be positioned on top of the SCARA 24. Light indicator 28 may illuminate as any type of light to indicate "conditions" in which automated medical system 2 is currently operating. For example, the illumination of green may indicate that all systems are normal. Illuminating red may indicate that automated medical system 2 is not operating normally. A pulsating light may mean automated medical system 2 is performing a function. Combinations of light and pulsation may create a nearly limitless amount of combinations in which to communicate the current operating "conditions." In embodiments, the light may be produced by LED bulbs, which may form a ring around light indicator 28. Light indicator 28 may comprise a fully permeable material that may let light shine through the entirety of light indicator 28. In embodiments, light indicator 28 may only allow a ring and/or designated sections of light indicator 28 to allow light to pass through.

Figure 2:
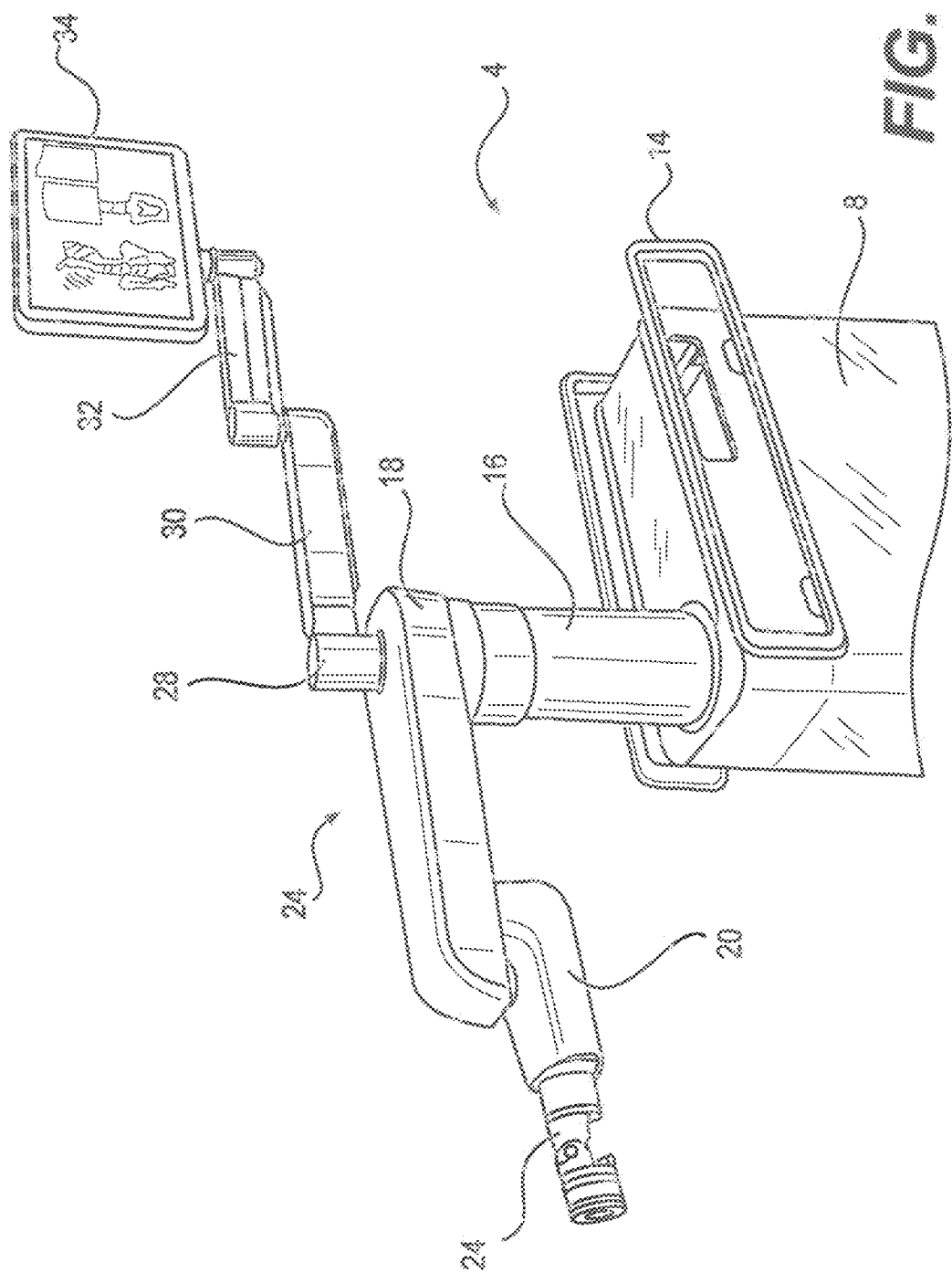
FIG. 2 illustrates an embodiment of a robot support system.

Light indicator 28 may be attached to lower display support 30. Lower display support 30, as illustrated in FIG. 2 may allow an operator to maneuver display 34 to any suitable location. Lower display support 30 may attach to light indicator 28 by any suitable means. Suitable means may be but is not limited to, latch, clamp, nuts and bolts, ball and socket fitting, press fitting, weld, adhesion, screws, rivets, and/or any combination thereof. In embodiments, lower display support 30 may rotate about light indicator 28. In embodiments, lower display support 30 may attach rigidly to light indicator 28. Light indicator 28 may then rotate three hundred and sixty degrees about robot support arm 18. Lower display support 30 may be of any suitable length, a suitable length may be about eight inches to about thirty four inches. Lower display support 30 may act as a base for upper display support 32.

Upper display support 32 may attach to lower display support 30 by any suitable means. Suitable means may be, but are not limited to, latch, clamp, nuts and bolts, ball and socket fitting, press fitting, weld, adhesion, screws, rivets, and/or any combination thereof. Upper display support 32 may be of any suitable length, a suitable length may be about eight inches to about thirty four inches. In embodiments, as illustrated in FIG. 1, upper display support 32 may allow display 34 to rotate three hundred and sixty degrees in relation to upper display support 32. Likewise, upper display support 32 may rotate three hundred and sixty degrees in relation to lower display support 30.

Display 34 may be any device which may be supported by upper display support 32. In embodiments, as illustrated in FIG. 2, display 34 may produce color and/or black and white images. The width of display 34 may be about eight inches to about thirty inches wide. The height of display 34 may be about six inches to about twenty two inches wide. The depth of display 34 may be about one half inch to about four inches.

In embodiments, a tablet may be used in conjunction with display 34 and/or without display 34. In embodiments, the table may be disposed on upper display support 32, in place of display 34, and may be removable from upper display support 32 during a medical operation. In addition the tablet may communicate with display 34. The table may be able to connect to robot support system 4 by any suitable wireless and/or wired connection. In embodiments, the tablet may be able to program and/or control automated medical system 2 during a medical operation. When controlling automated medical system 2 with the tablet, all input and output commands may be duplicated on display 34. The use of a tablet may allow an operator to manipulate robot support system 4 without having to move around patient 50 and/or to robot support system 4.

Figure 5:
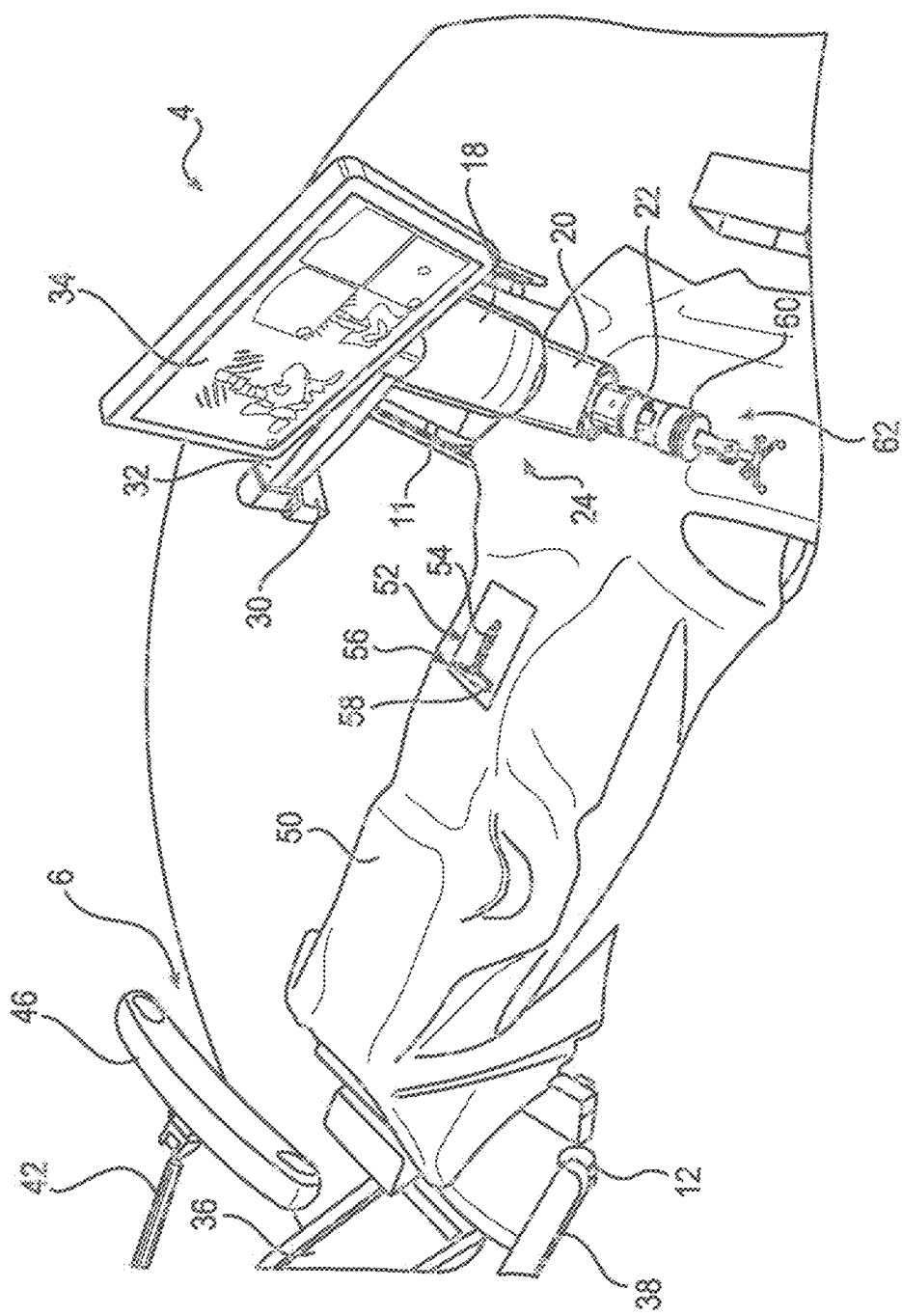
FIG. 5 illustrates an embodiment of a medical operation in which a robot support system and a camera system are disposed around a patient.

As illustrated in FIG. 5, camera tracking system 6 may work in conjunction with robot support system 4. Described above, camera tracking system 6 and robot support system 4 may be able to attach to each other. Camera tracking system 6, now referring to FIG. 1, may comprise similar components of robot support system 4. For example, camera body 36 may provide the functionality found in robot body 8. Robot body 8 may provide the structure upon which camera 46 may be mounted. The structure within robot body 8 may also provide support for the electronics, communication devices, and power supplies used to operate camera tracking system 6. Camera body 36 may be made of the same material as robot body 8. Camera tracking system 6 may also communicate with robot support system 4 by any suitable means. Suitable means may be, but are not limited to, a wired or wireless connection. Additionally, camera tracking system 6 may communicate directly to the table by a wireless and/or wired connection. This communication may allow the tablet to control the functions of camera tracking system 6.

Camera body 36 may rest upon camera base 38. Camera base 38 may function as robot base 10. In embodiments, as illustrated in FIG. 1, camera base 38 may be wider than robot base 10. The width of camera base 38 may allow for camera tracking system 6 to connect with robot support system 4. As illustrated in FIG. 1, the width of camera base 38 may be large enough to fit outside robot base 10. When camera tracking system 6 and robot support system 4 are connected, the additional width of camera base 38 may allow automated medical system 2 additional maneuverability and support for automated medical system 2.

As with robot base 10, a plurality of powered wheels 12 may attach to camera base 38. Powered wheel 12 may allow camera tracking system 6 to stabilize and level or set fixed orientation in regards to patient 50, similar to the operation of robot base 10 and powered wheels 12. This stabilization may prevent camera tracking system 6 from moving during a medical procedure and may keep camera 46 from losing track of DRA 52 within a designated area. This stability and maintenance of tracking may allow robot support system 4 to operate effectively with camera tracking system 6. Additionally, the wide camera base 38 may provide additional support to camera tracking system 6. Specifically, a wide camera base 38 may prevent camera tracking system 6 from tipping over when camera 46 is disposed over a patient, as illustrated in FIG. 5. Without the wide camera base 38, the outstretched camera 46 may unbalance camera tracking system 6, which may result in camera tracking system 6 falling over.

Camera telescoping support 40 may support camera 46. In embodiments, telescoping support 40 may move camera 46 higher or lower in the vertical direction. Telescoping support 40 may be made of any suitable material in which to support camera 46. Suitable material may be, but is not limited to, metal such as titanium, aluminum, or stainless steel, carbon fiber, fiberglass, or heavy-duty plastic. Camera handle 48 may be attached to camera telescoping support 40 at any suitable location. Cameral handle 48 may be any suitable handle configuration. A suitable configuration may be, but is not limited to, a bar, circular, triangular, square, and/or any combination thereof. As illustrated in FIG. 1, camera handle 48 may be triangular, allowing an operator to move camera tracking system 6 into a desired position before a medical operation. In embodiments, camera handle 48 may be used to lower and raise camera telescoping support 40. Camera handle 48 may perform the raising and lowering of camera telescoping support 40 through the depression of a button, switch, lever, and/or any combination thereof.

Lower camera support arm 42 may attach to camera telescoping support 40 at any suitable location, in embodiments, as illustrated in FIG. 1, lower camera support arm 42 may rotate three hundred and sixty degrees around telescoping support 40. This free rotation may allow an operator to position camera 46 in any suitable location. Lower camera support arm 42 may be made of any suitable material in which to support camera 46. Suitable material may be, but is not limited to, metal such as titanium, aluminum, or stainless steel, carbon fiber, fiberglass, or heavy-duty plastic. Cross-section of lower camera support arm 42 may be any suitable shape. Suitable cross-sectional shape may be, but is not limited to, circle, square, rectangle, hexagon, octagon, or i-beam. The cross-sectional length and width may be about one to ten inches. Length of the lower camera support arm may be about four inches to about thirty-six inches. Lower camera support arm 42 may connect to telescoping support 40 by any suitable means. Suitable means may be, but is not limited to, nuts and bolts, ball and socket fitting, press fitting, weld, screws, and/or any combination thereof. Lower camera support arm 42 may be used to provide support for camera 46. Camera 46 may be attached to lower camera support arm 42 by any suitable means. Suitable means may be, but is not limited to, nuts and bolts, ball and socket fitting, press fitting, weld, screws, and/or any combination thereof. Camera 46 may pivot in any direction at the attachment area between camera 46 and lower camera support arm 42. In embodiments a curved rail 44 may be disposed on lower camera support arm 42.

Figure 3:
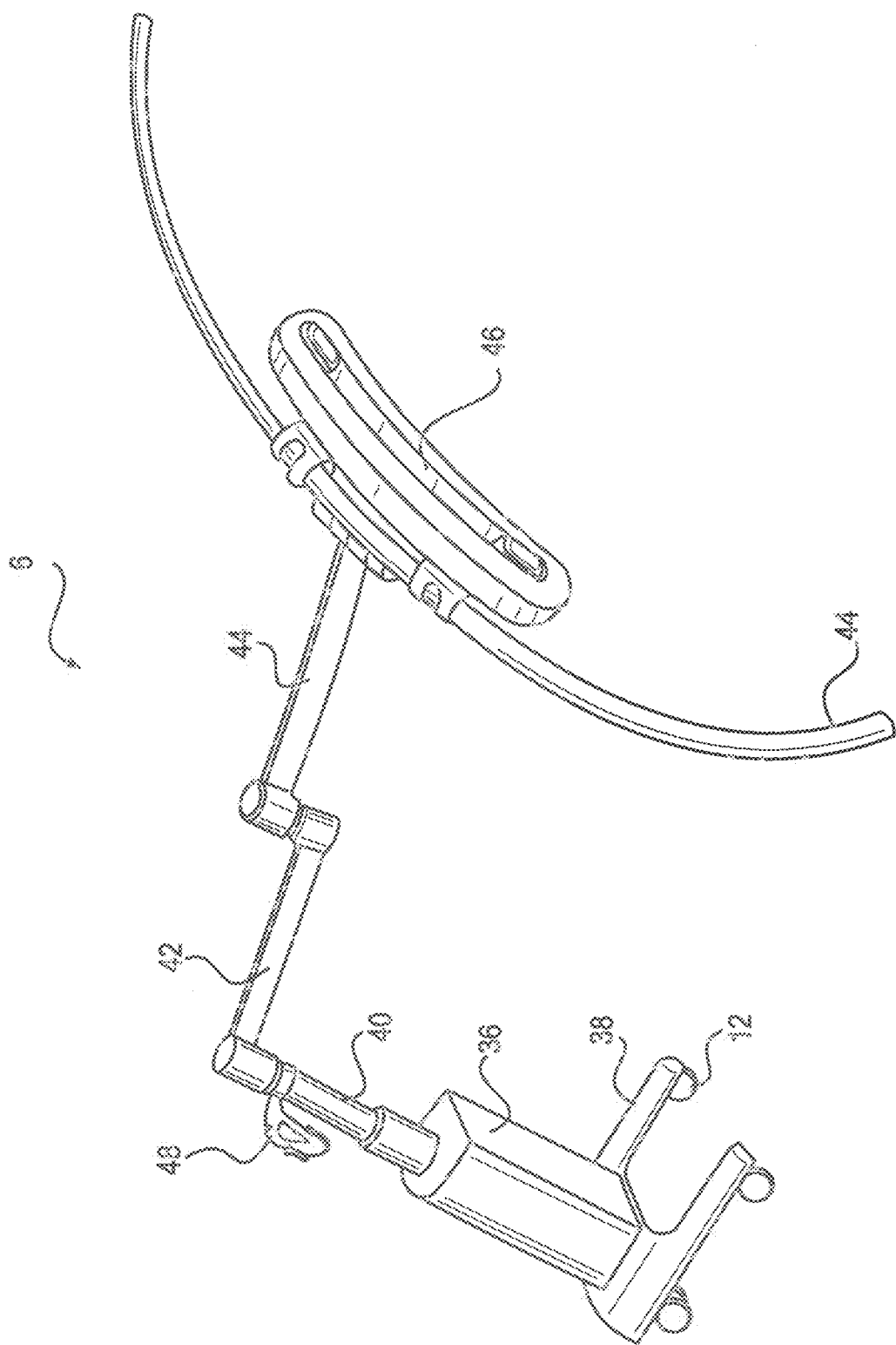
FIG. 3 illustrates an embodiment of a camera tracking system.

Curved rail 44 may be disposed at any suitable location on lower camera support arm 42. As illustrated in FIG. 3, curved rail 44 may attach to lower camera support arm 42 by any suitable means. Suitable means may be, but are not limited to nuts and bolts, ball and socket fitting, press fitting, weld, adhesion, screws, rivets, clamps, latches, and/or any combination thereof. Curved rail 44 may be of any suitable shape, a suitable shape may be a crescent, circular, oval, elliptical and/or any combination thereof. In embodiments, curved rail 44 may be any appropriate length. An appropriate length may be about one foot to about six feet. Camera 46 may be moveably disposed along curved rail 44. Camera 46 may attach to curved rail 44 by any suitable means. Suitable means may be, but are not limited to rollers, brackets, braces, motors, and/or any combination thereof. Motors and rollers, not illustrated, may be used to move camera 46 along curved rail 44. As illustrated in FIG. 3, during a medical procedure, if an object prevents camera 46 from viewing one or more DRAs 52, the motors may move camera 46 along curved rail 44 using rollers. This motorized movement may allow camera 46 to move to a new position that is no longer obstructed by the object without moving camera tracking system 6. While camera 46 is obstructed from viewing DRAs 52, camera tracking system 6 may send a stop signal to robot support system 4, display 34, and/or a tablet. The stop signal may prevent SCARA 24 from moving until camera 46 has reacquired DRAs 52. This stoppage may prevent SCARA 24 and/or end effector 22 from moving and/or using medical tools without being tracked by automated medical system 2.

Figure 6:
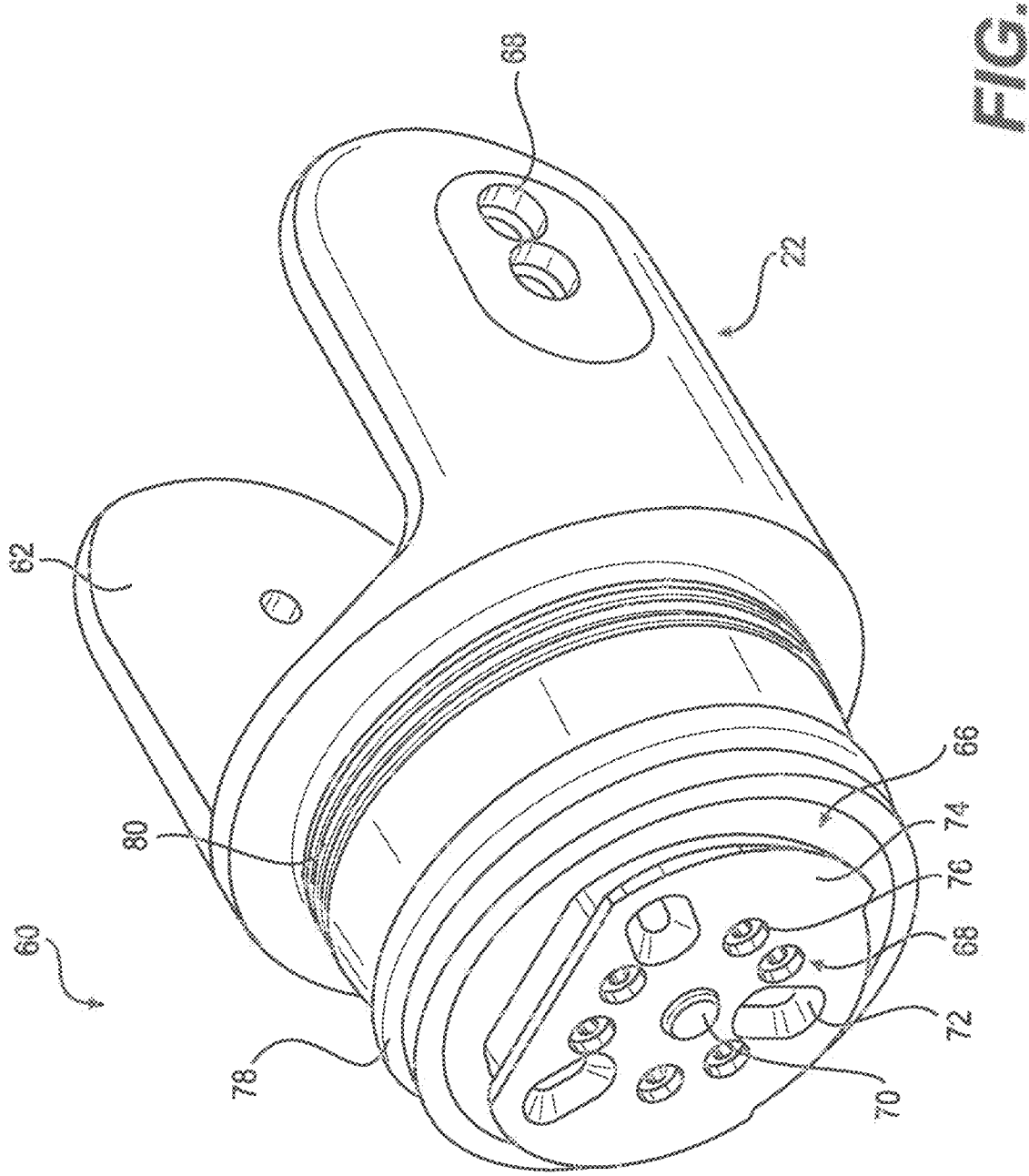
FIG. 6 illustrates an embodiment of an end effector.

End effector 22, as illustrated in FIG. 6, may be used to connect surgical tools to robot support system 4. End effector 22 may comprise a saddle joint 62, an activation assembly 60, a load cell 64, and a tool connection 66. Saddle joint 62 may attach end effector 22 to SCARA 24. Saddle joint 62 may be made of any suitable material. Suitable material may be, but is not limited to metal such as titanium, aluminum, or stainless steel, carbon fiber, fiberglass, or heavy-duty plastic. Saddle joint 62 may be made of a single piece of metal which may provide end effector with additional strength and durability. In examples saddle joint 62 may attach to SCARA 24 by an attachment point 68. There may be a plurality of attachment points 68 disposed about saddle joint 62. Attachment points 68 may be sunk, flush, and/or disposed upon saddle joint 62. In examples, screws, nuts and bolts, and/or any combination thereof may pass through attachment point 68 and secure saddle joint 62 to SCARA 24. The nuts and bolts may connect saddle joint 62 to a motor, not illustrated, within SCARA 24. The motor may move saddle joint 62 in any direction. The motor may further prevent saddle joint 62 from moving from accidental bumps and/or accidental touches by actively servoing at the current location or passively by applying spring actuated brakes. Saddle joint 62 may provide the base upon which a load cell 64 and a tool connection 66 may be disposed.

Figure 7:
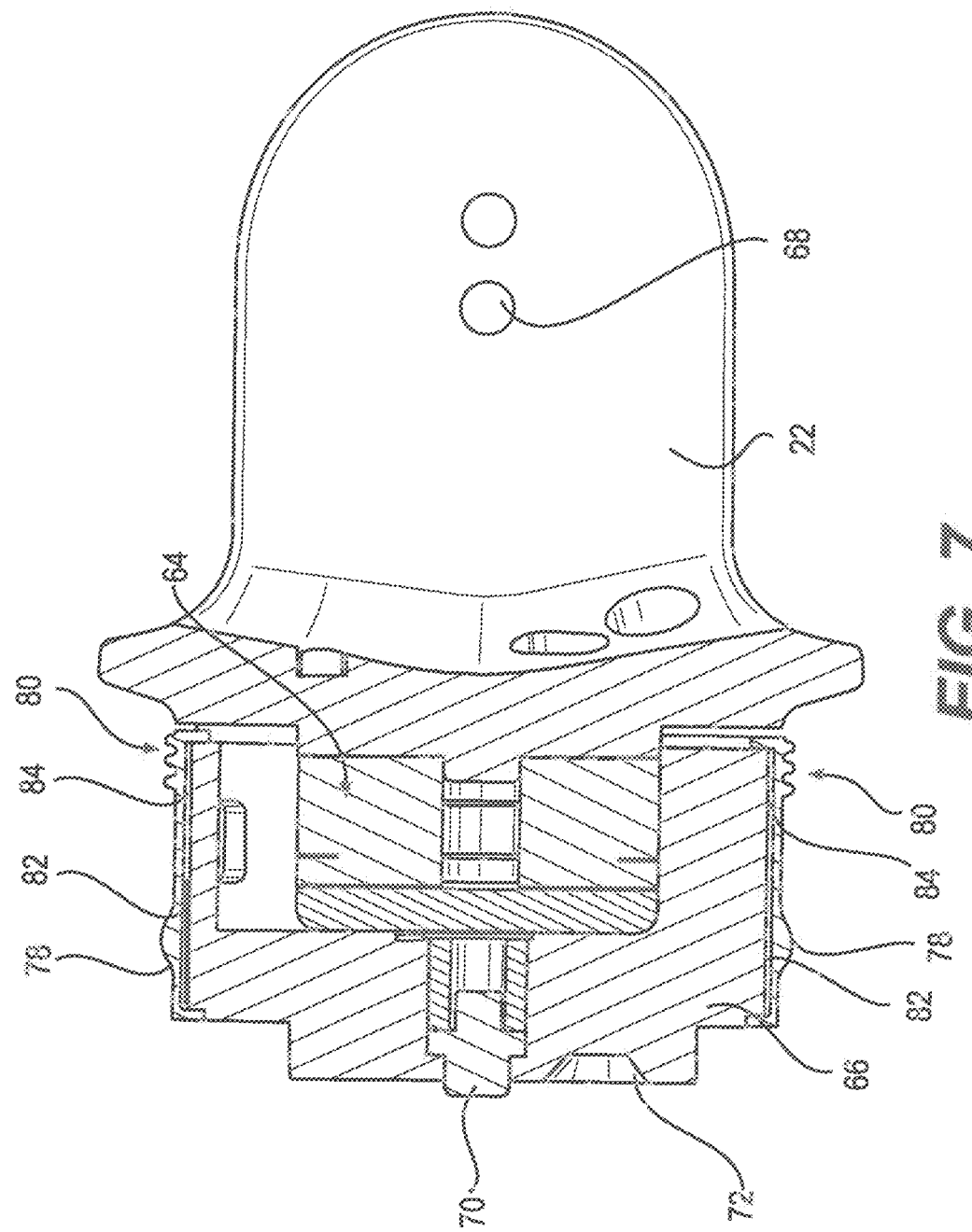
FIG. 7 illustrates an embodiment of a cut away of an end effector.
Figure 8:
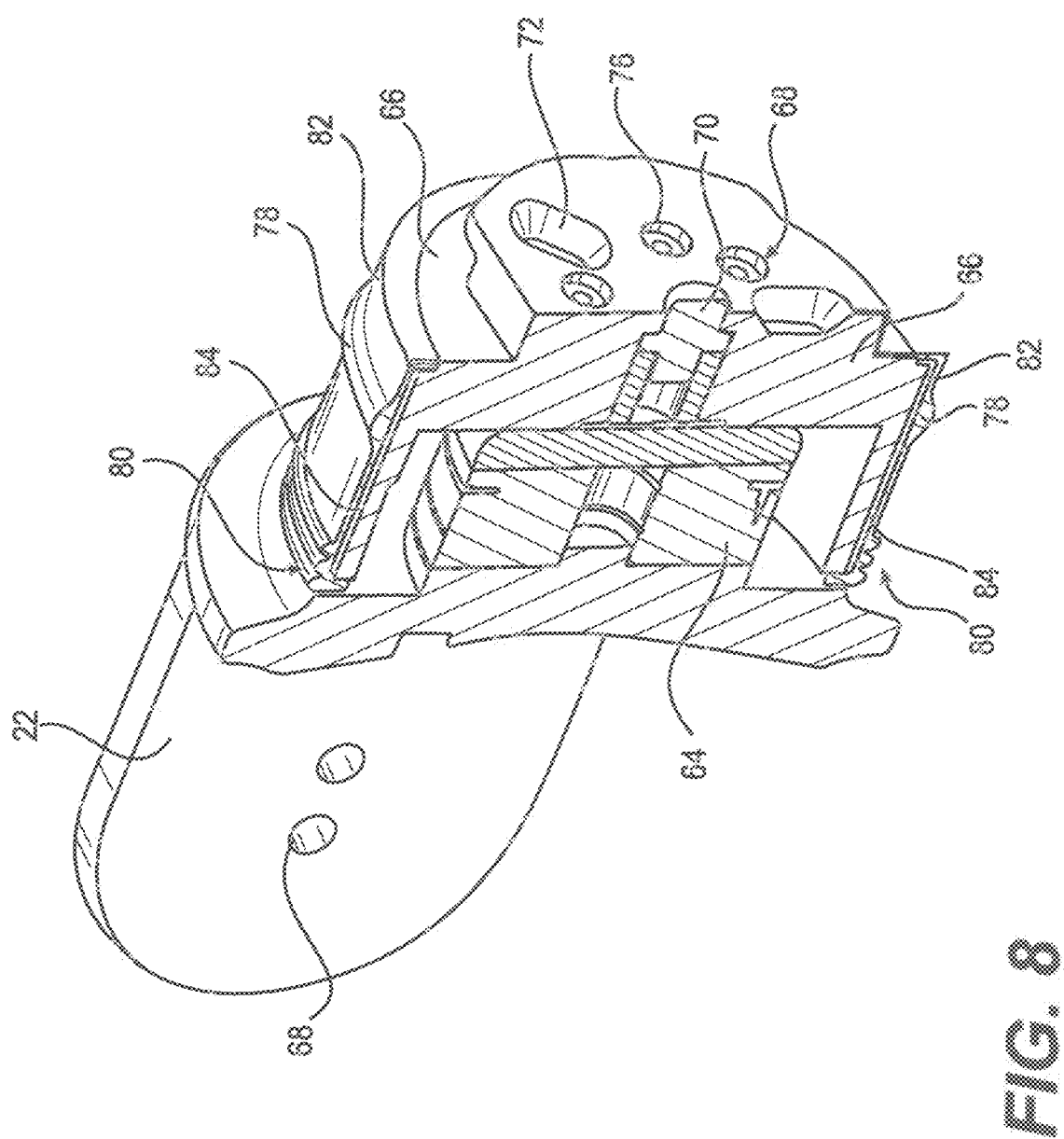
FIG. 8 illustrates an embodiment of a perspective view of an end effector cut away.
Figure 17:
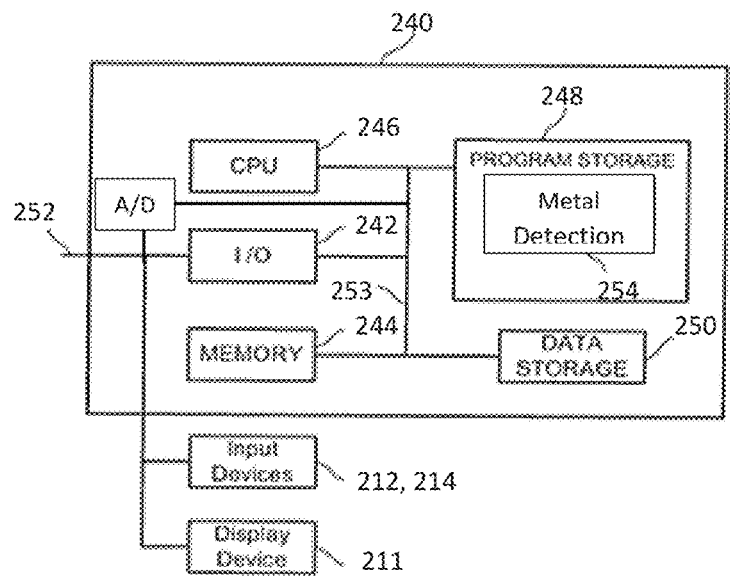
FIG. 17 is a schematic diagram of a controller for detecting a metal object, such as an instrument positioned in the tube portion of the end effector tool according to an aspect of the present invention.

Load cell 64, as illustrated in FIGS. 7 and 8 may attach to saddle joint 62 by any suitable means. Suitable means may be, but is not limited to, screws, nuts and bolts, threading, press fitting, and/or any combination thereof. Load cell 64 may be any suitable instrument used to detect and measurement movement. In examples, load cell 64 may be a six axis load cell, a three-axis load cell or a uniaxial load cell. Load cell 64 may be used to track the force applied to end effector 22. As illustrated in FIG. 17, a schematic may show the communication between load cell 64 and a motor 120. In embodiments a load cell 64 may communicate with a plurality of motors 120. As load cell 64 senses pressure, information as to the amount of force applied may be distributed from a switch array 122 and/or a plurality of switch arrays to a microcontroller unit 122. Microcontroller unit 124 may take the force information from load cell 64 and process it with a switch algorithm. The switch algorithm may allow microcontroller unit 124 to communicate with a motor driver 126. A motor driver 126 may control the function of a motor 120, with which motor driver 126 may communicate with. Motor driver 126 may direct specific motors 120 to produce an equal amount of force measured by load cell 64 through motor 120. In embodiments, the force produced may come from a plurality of motors 120, as directed by microcontroller unit 124. Additionally, motor driver 126 may receive input from motion controller 128. Motion controller 128 may receive information from load cell 64 as to the direction of force sensed by load cell 64. Motion controller 128 may process this information using a motion controller algorithm. The algorithm may be used to provide information to specific motor drivers 126. To replicate the direction of force, motion controller 128 may activate and/or deactivate certain motor drivers 126. Working in unison and/or separately, microcontroller unit 124 and motion controller 128 may control motor 120 (or a plurality of motors 120) to induce in the direction the motion and direction of force sensed by load cell 64. This force-controlled motion may allow an operator to move SCARA 24 and end effector 22 effortlessly and/or with very little resistance. Movement of end effector 22 may position tool connection 66 in any suitable location for use by medical personnel.

Tool connection 66 may attach to load cell 64. Tool connection 66 may comprise attachment points 68, a sensory button 70, tool guides 72, and/or tool connections 74. Best illustrated in FIGS. 6 and 8, there may be a plurality of attachment points 68. Attachment points 68 may connect tool connection 66 to load cell 64. Attachment points 68 may be sunk, flush, and/or disposed upon tool connection 66. Connectors 76 may use attachment points 68 to attach tool connection 66 to load cell 64. In examples, connectors 76 may be screws, nuts and bolts, press fittings, and/or any combination thereof.

As illustrated in FIG. 6, a sensory button 70 may be disposed about center of tool connection 66. Sensory button 70 may be depressed when an end effector tool 26, best illustrated in FIG. 4, is connected to end effector 22. Depression of sensory button 70 may alert robot support system 4, and in turn medical personnel, that an end effector tool 26 has been attached to end effector 22. As illustrated in FIG. 6, tool guides 72 may be used to facilitate proper attachment of end effector tool 26 to end effector 22. Tool guides 72 may be sunk, flush, and/or disposed upon tool connection 66. In examples there may be a plurality of tool guides 72 and may have any suitable patterns and may be oriented in any suitable direction. Tool guides 72 may be any suitable shape to facilitate attachment of end effector tool 26 to end effector 22. A suitable shape may be, but is not limited to, circular, oval, square, polyhedral, and/or any combination thereof. Additionally, tool guides 72 may be cut with a bevel, straight, and/or any combination thereof.

Tool connection 66 may have attachment points 74. As illustrated in FIG. 6, attachment points 74 may form a ledge and/or a plurality of ledges. Attachment points 74 may provide end effector tool 26 a surface upon which end effector tool 26 may clamp. In examples, attachment points 74 may be disposed about any surface of tool connection 66 and oriented in any suitable manner in relation to tool connection 66.

Tool connection 66 may further serve as a platform for activation assembly 60. Activation assembly 60, best illustrated in FIGS. 6 and 8, may encircle tool connection 66. In embodiments, activation assembly 60 may take the form of a bracelet. As bracelet, activation assembly 60 may wrap around tool connection 66. In embodiments, activation assembly 60, may be located in any suitable area within automated medical system 2. In examples, activation assembly 60 may be located on any part of SCARA 24, any part of end effector 22, may be worn by medical personnel (and communicate wirelessly), and/or any combination thereof. Activation assembly 60 may be made of any suitable material. Suitable material may be, but is not limited to neoprene, plastic, rugger, gel, carbon fiber, fabric and/or any combination thereof. Activation assembly 60 may comprise of a primary button 78 and a secondary button 80. Primary button 78 and secondary button 80 may encircle the entirety of tool connection 66. Primary button 78 may be a single ridge, as illustrated in FIG. 6, which may encircle tool connection 66. In examples, primary button 78 may be disposed upon activation assembly 60 along the end farthest away from saddle joint 62. Primary button 78 may be disposed upon primary activation switch 82, best illustrated on FIG. 7. Primary activation switch 82 may be disposed between tool connection 66 and activation assembly 60. In examples, there may be a plurality of primary activation switches 82, which may be disposed adjacent and beneath primary button 78 along the entire length of primary button 78. Depressing primary button 78 upon primary activation switch 82 may allow an operator to move SCARA 24 and end effector 22. As discussed above, once set in place, SCARA 24 and end effector 22 may not move until an operator programs robot support system 4 to move SCARA 24 and end effector 22, or is moved using primary button 78 and primary activation switch 82. In examples, it may require the depression of at least two non-adjacent primary activation switches 82 before SCARA 24 and end effector 22 will respond to commands. Depression of at least two primary activation switches 82 may prevent the accidental movement of SCARA 24 and end effector 22 during a medical procedure.

Activated by primary button 78 and primary activation switch 82, load cell 64 may measure the force magnitude and/or direction of force exerted upon end effector 22 by medical personnel. This information may be transferred to motors within SCARA 24 that may be used to move SCARA 24 and end effector 22. Information as to the magnitude and direction of force measured by load cell 64 may cause the motors to move SCARA 24 and end effector 22 in the same direction as sensed by load cell 64. This force controlled movement may allow the operator to move SCARA 24 and end effector 22 easily and without large amounts of exertion due to the motors moving SCARA 24 and end effector 22 at the same time the operator is moving SCARA 24 and end effector 22.

Secondary button 80, as illustrated in FIG. 6, may be disposed upon the end of activation assembly 60 closest to saddle joint 62. In examples secondary button 80 may comprise a plurality of ridges. The plurality of ridges may be disposed adjacent to each other and may encircle tool connection 66. Additionally, secondary button 80 may be disposed upon secondary activation switch 84. Secondary activation switch 84, as illustrated in FIG. 7, may be disposed between secondary button 80 and tool connection 66. In examples, secondary button 80 may be used by an operator as a "selection" device. During a medical operation, robot support system 4 may notify medical personnel to certain conditions by display 34 and/or light indicator 28. Medical personnel may be prompted by robot support system 4 to select a function, mode, and/or asses the condition of automated medical system 2. Depressing secondary button 80 upon secondary activation switch 84 a single time may activate certain functions, modes, and/or acknowledge information communicated to medical personnel through display 34 and/or light indicator 28. Additionally, depressing secondary button 80 upon secondary activation switch 84 multiple times in rapid succession may activate additional functions, modes, and/or select information communicated to medical personnel through display 34 and/or light indicator 28. In examples, at least two non-adjacent secondary activation switches 84 may be depressed before secondary button 80 may function properly. This requirement may prevent unintended use of secondary button 80 from accidental bumping by medical personnel upon activation assembly 60. Primary button 78 and secondary button 80 may use software architecture 86 to communicate commands of medical personnel to automated medical system 2.

Figure 9:
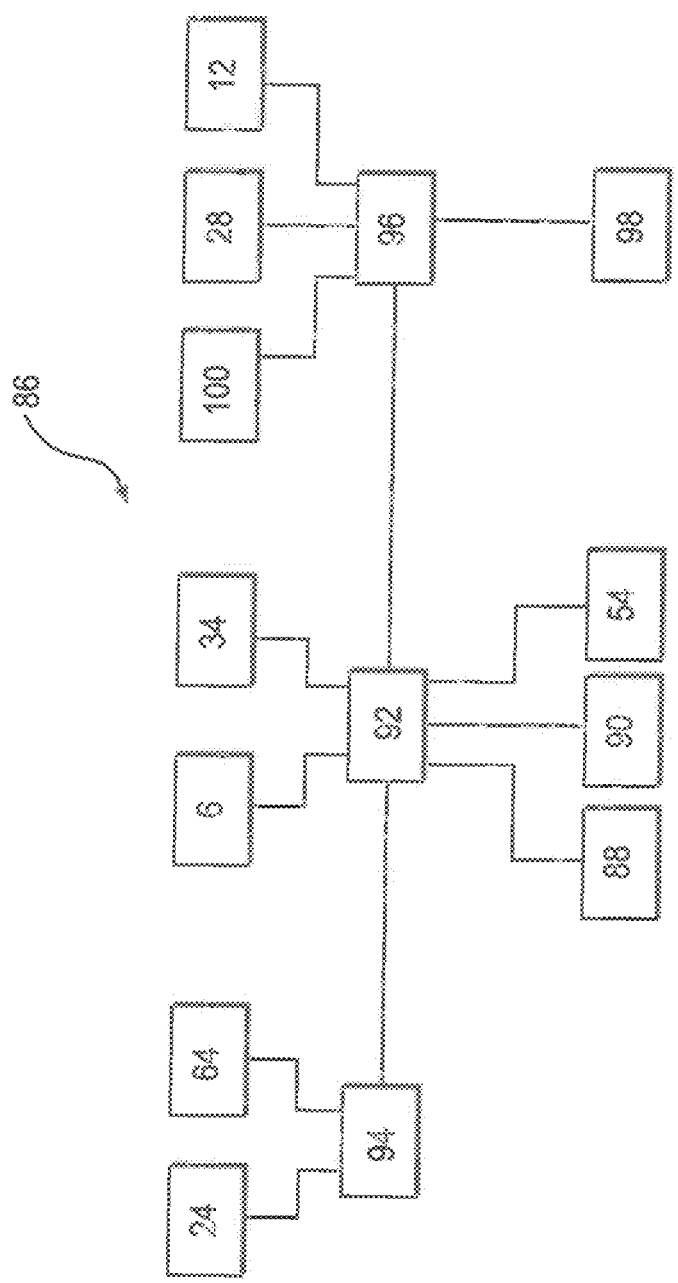
FIG. 9 illustrates an embodiment of a schematic of software architecture used in an automated medical system.

FIG. 9 illustrates a flow chart of software architecture 86 which may be used within automated medical system 2. Software architecture 86 may be used to automated robot support system 4 and camera tracking system 6. Additionally, software architecture 86 may allow an operator to manipulate automated medical system 2 based upon commands given from the operator. In examples, operator commands may comprise Picture Archival and Communication Systems (PACS) 88 (which may communicate with automated imaging system 104, discussed below), USB Devices 90, and commands from tablet 54. These operator commands may be received and transferred throughout automated medical system 2 by a computer processor 92. Computer processor 92 may be able to receive all commands and manipulate automated medical system 2 accordingly. In examples, computer processor 92 may be able to control and identify the location of individual parts that comprise automated medical system 2. Communicating with camera tracking system 6 and display 34, computer processor 92 may be able to locate a patient, end effector 22, and robot support system 4 in a defined space (e.g., illustrated in FIG. 5). Additionally, computer processor 92 may be able to use commands from display 34 and camera tracking system 6 to alter the positions of SCARA 24. Information from load cell 64, based upon measured force magnitude and direction, may be processed by computer processor 92 and sent to motors within SACARA 24, as discussed above. A General Algebraic Modeling System (GAMS) 94 may translate information regarding force magnitude from load cell 64 to electronic signals which may be useable by computer processor 92. This translation may allow computer processor 92 to track the location and movement of robot support system 4 in a defined space when SCARA 24 and end effector 22 are moving. Computer processor 92 may further use firmware 96 to control commands and signals from robot body 8. Firmware 96 may comprise commands that are hardwired to automated medical system 2. For example, computer processor 92 may require power from power supply 98 to operate. Firmware 96 may control the distribution of power from power supply 98 to automated medical system 2. Additionally, computer processor 92 may control firmware 96 and the power distribution based on operator commands. In examples, firmware 96 may communicate with light indicator 28, powered wheels 12, and platform interface 100. Platform interface 100 may be a series of hardwired button commands that directly control automated medical system 2. Buttons commands are not limited to but may comprise functions that may move automated medical system 2 in any direction, initiate an emergency stop, initiate movement of SCARA 24, and/or communicate current system functionality to medical personnel. Computer processor 92 may process and distribute all operator commends to perform programmed tasks by medical personnel.

Figure 10:
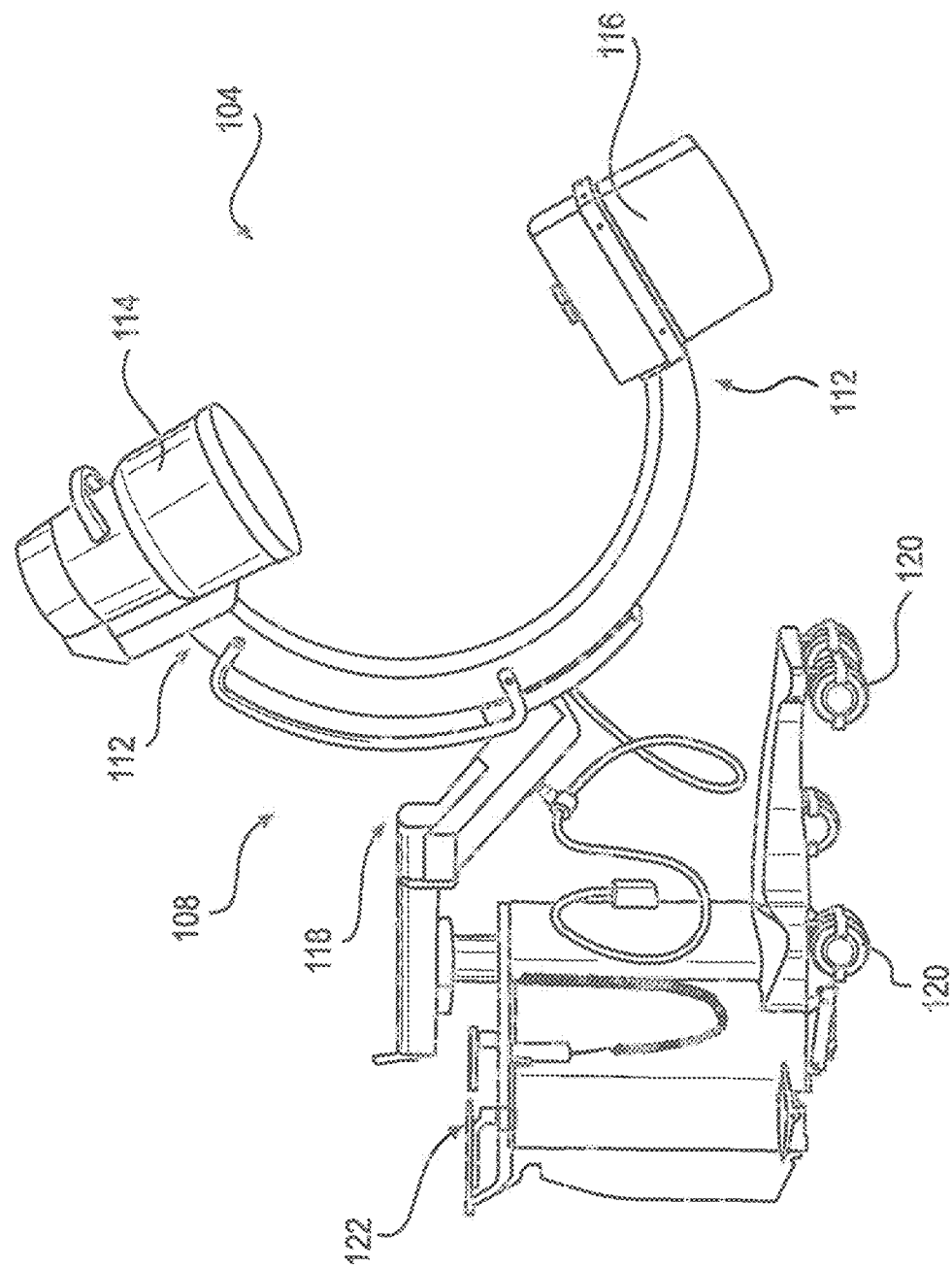
FIG. 10 illustrates an embodiment of a C-Arm imaging device.

Automated imaging system 104 may be used in conjunction with automated medical system 2 to acquire pre-operative, intra-operative, post-operative, and/or real-time image data of patient 50. Any appropriate subject matter may be imaged for any appropriate procedure using automated imaging system 104. In embodiments, automated imaging system 104 may be an any imaging device such as imaging device 106 and/or a C-arm 108 device. It may be desirable to take x-rays of patient 50 from a number of different positions, without the need for frequent manual repositioning of patient 50 which may be required in an x-ray system. C-arm 108 x-ray diagnostic equipment may solve the problems of frequent manual repositioning and may be well known in the medical art of surgical and other interventional procedures. As illustrated in FIG. 10, a C-arm 108 may comprise an elongated C-shaped member 110 terminating in opposing distal ends 112 of the "C" shape. C-shaped member 110 may further comprise an x-ray source 114 and an image receptor 116, which may be mounted at or near distal ends 112, respectively, of C-arm 108 in opposing orientation, with C-arm 108 supported in a suspended position. The space within C-arm 108 of the arm may provide room for the physician to attend to the patient substantially free of interference from x-ray support structure 118. X-ray support structure 118 may rest upon wheels 120, which may enable C-arm 108 to be wheeled from room to room and further along the length of patient 50 during a medical procedure. X-ray images produced from C-arm 108 may be used in an operating room environment to help ensure that automated medial system 2 may be properly positioned during a medical procedure.

C-arm 108 may be mounted to enable rotational movement of the arm in two degrees of freedom, (i.e. about two perpendicular axes in a spherical motion). C-arm 108 may be slidably mounted to x-ray support structure 118, which may allow orbiting rotational movement of C-arm 108 about its center of curvature, which may permit selective orientation of x-ray source 114 and image receptor 116 vertically and/or horizontally. C-arm 108 may also be laterally rotatable, (i.e. in a perpendicular direction relative to the orbiting direction to enable selectively adjustable positioning of x-ray source 114 and image receptor 116 relative to both the width and length of patient 50). Spherically rotational aspects of C-arm 108 apparatus may allow physicians to take x-rays of patient 50 at an optimal angle as determined with respect to the particular anatomical condition being imaged. In embodiments a C-arm 108 may be supported on a wheeled support cart 120. In embodiments imaging device 106 may be used separately and/or in conjunction with C-arm 108.

Figure 11:
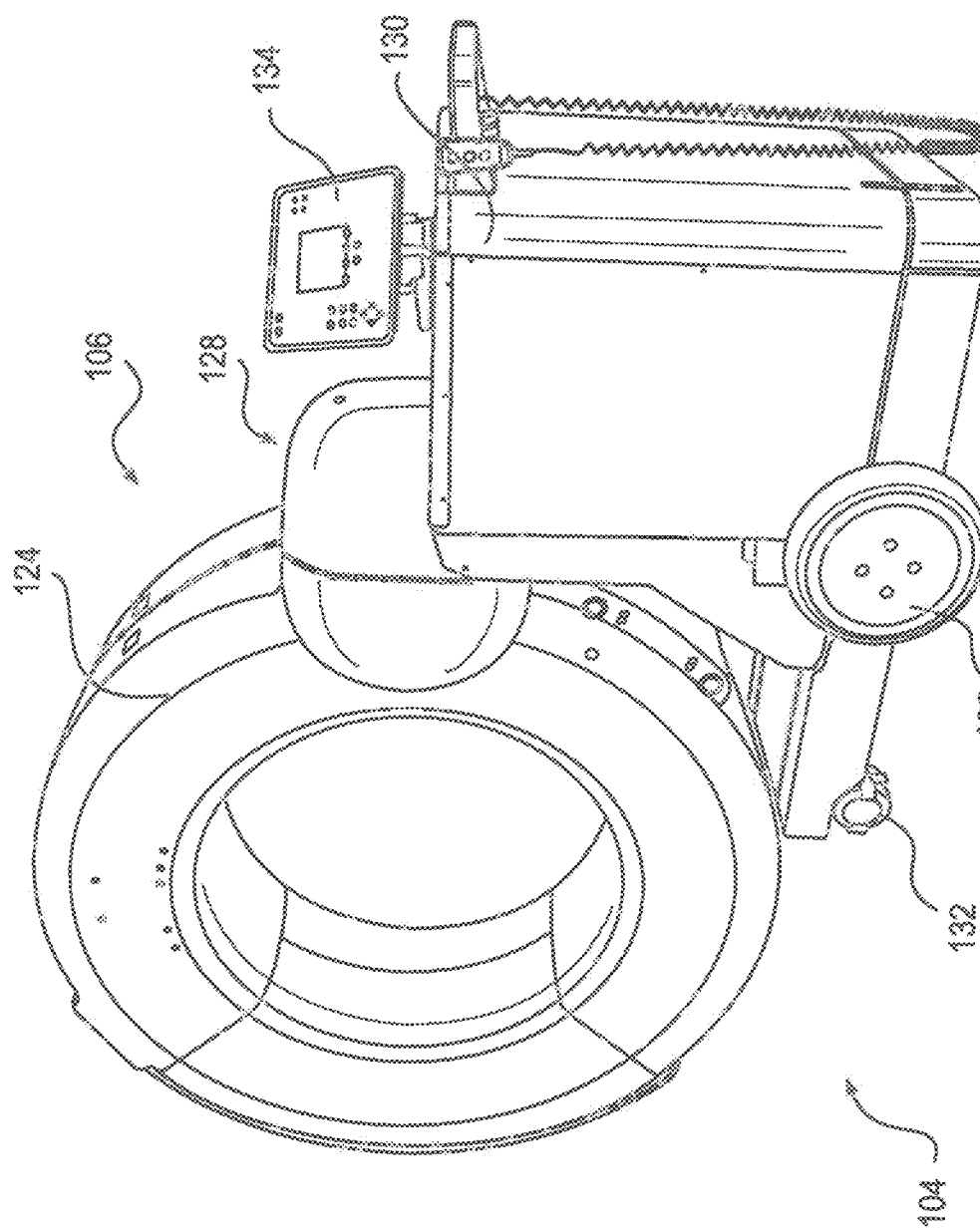
FIG. 11 illustrates an embodiment of an imaging device.

An imaging device 106, as illustrated in FIG. 11, may comprise a gantry housing 124, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 50 to be acquired from multiple directions or in multiple planes.

In embodiments imaging device 106 may comprises a gantry housing 124 having a central opening 126 for positioning around an object to be imaged, a source of radiation that is rotatable around the interior of gantry housing 124, which may be adapted to project radiation from a plurality of different projection angles. A detector system may be adapted to detect the radiation at each projection angle to acquire object images from multiple projection planes in a quasi-simultaneous manner. In embodiments, a gantry may be attached to a support structure imaging device support structure 128, such as a wheeled mobile cart 130 with wheels 132, in a cantilevered fashion. A positioning unit 134 may translate and/or tilt the gantry to a desired position and orientation, preferably under control of a computerized motion control system. The gantry may include a source and detector disposed opposite one another on the gantry. The source and detector may be secured to a motorized rotor, which may rotate the source and detector around the interior of the gantry in coordination with one another. The source may be pulsed at multiple positions and orientations over a partial and/or full three hundred and sixty degree rotation for multi-planar imaging of a targeted object located inside the gantry. The gantry may further comprise a rail and bearing system for guiding the rotor as it rotates, which may carry the source and detector. Both and/or either imaging device 106 and C-arm 108 may be used as automated imaging system 104 to scan patient 50 and send information to automated medical system 2.

Automated imaging system 104 may communicate with automated medical system 2 before, during, and/or after imaging has taken place. Communication may be performed through hard wire connections and/or wireless connections. Imaging may be produced and sent to automated medical system 2 in real time. Images captured by automated imaging system 104 may be displayed on display 34, which may allow medical personal to locate bone and organs within a patient. This may further allow medical personnel to program automated medial system 2 to assist during a medical operation.

Figure 12:
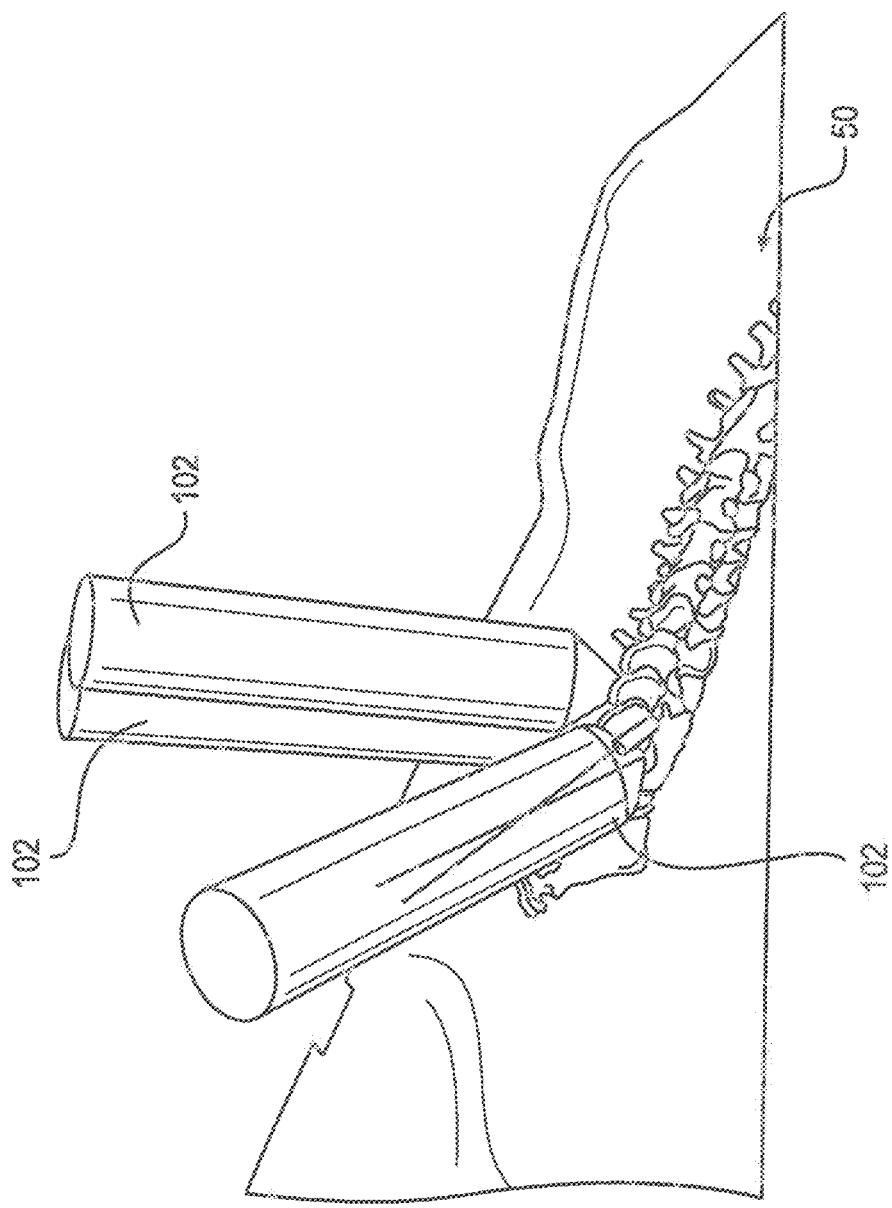
FIG. 12 illustrates an embodiment of a gravity well for a medical procedure.

During a medical operation, medical personnel may program robot support system 4 to operate within defined specifications. For examples, as illustrated in FIG. 12, a patient 50 may have a medical procedure performed upon the spine. Medical personnel may use imaging equipment to locate and find the spine, as detailed above. Using the images, an operator may upload the information regarding the location of the spine into automated medical system 2. Automated medical system 2 may then track, locate, and move end effector tools 26 to areas specified by the operator. In an example, a gravity well 102 and/or a plurality of gravity wells 102 may be mapped onto the spine of patient 50, as illustrated in FIG. 12. Gravity wells 102 may be areas, programmed by an operator, to attract end effector tools 26. These areas may cause SCARA 24 and end effector 22 to move toward the direction, angle, and location programmed by medical personnel.

Figure 13:
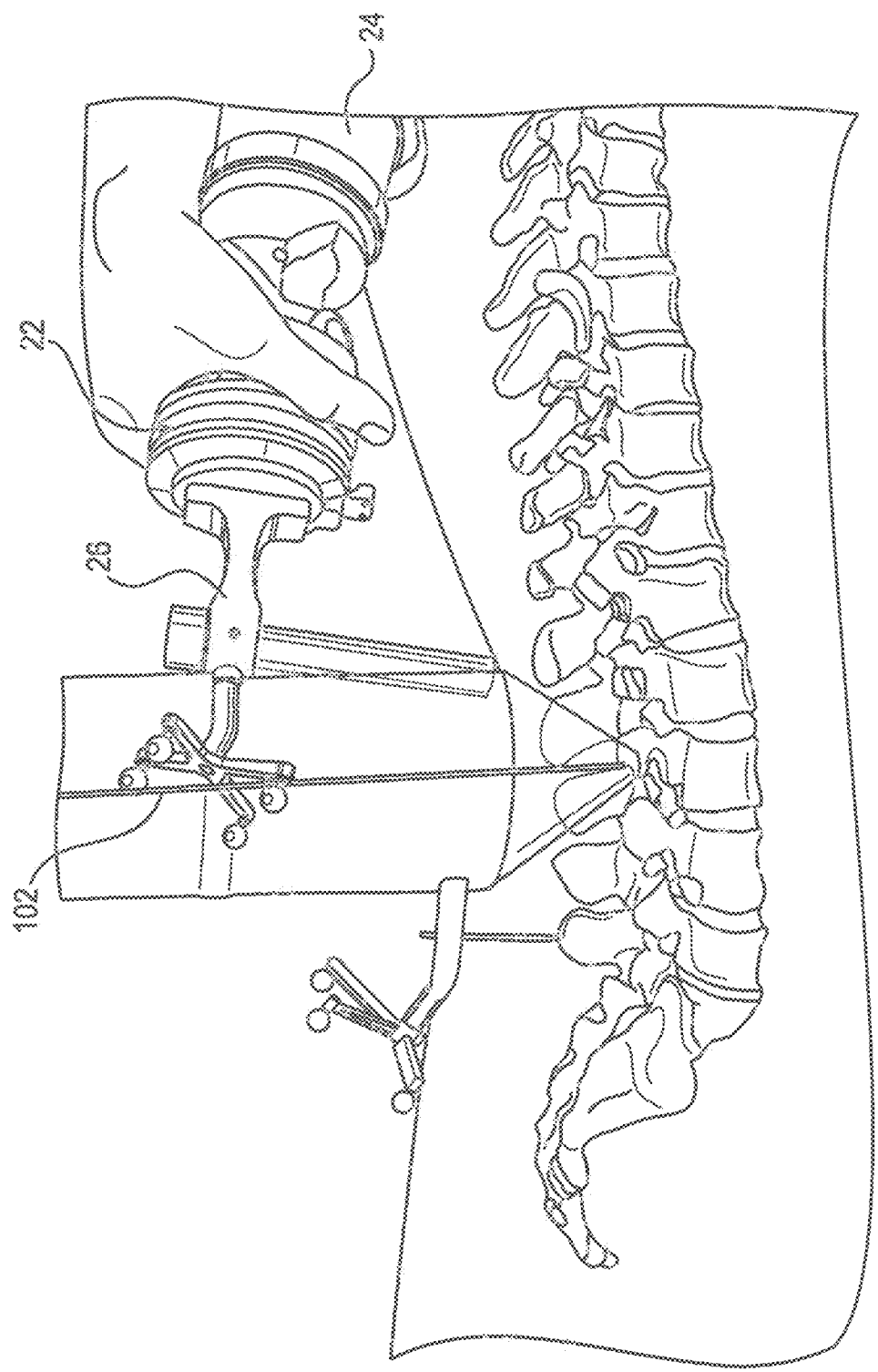
FIG. 13 illustrates an embodiment of an end effector tool moving toward a gravity well.
Figure 14:
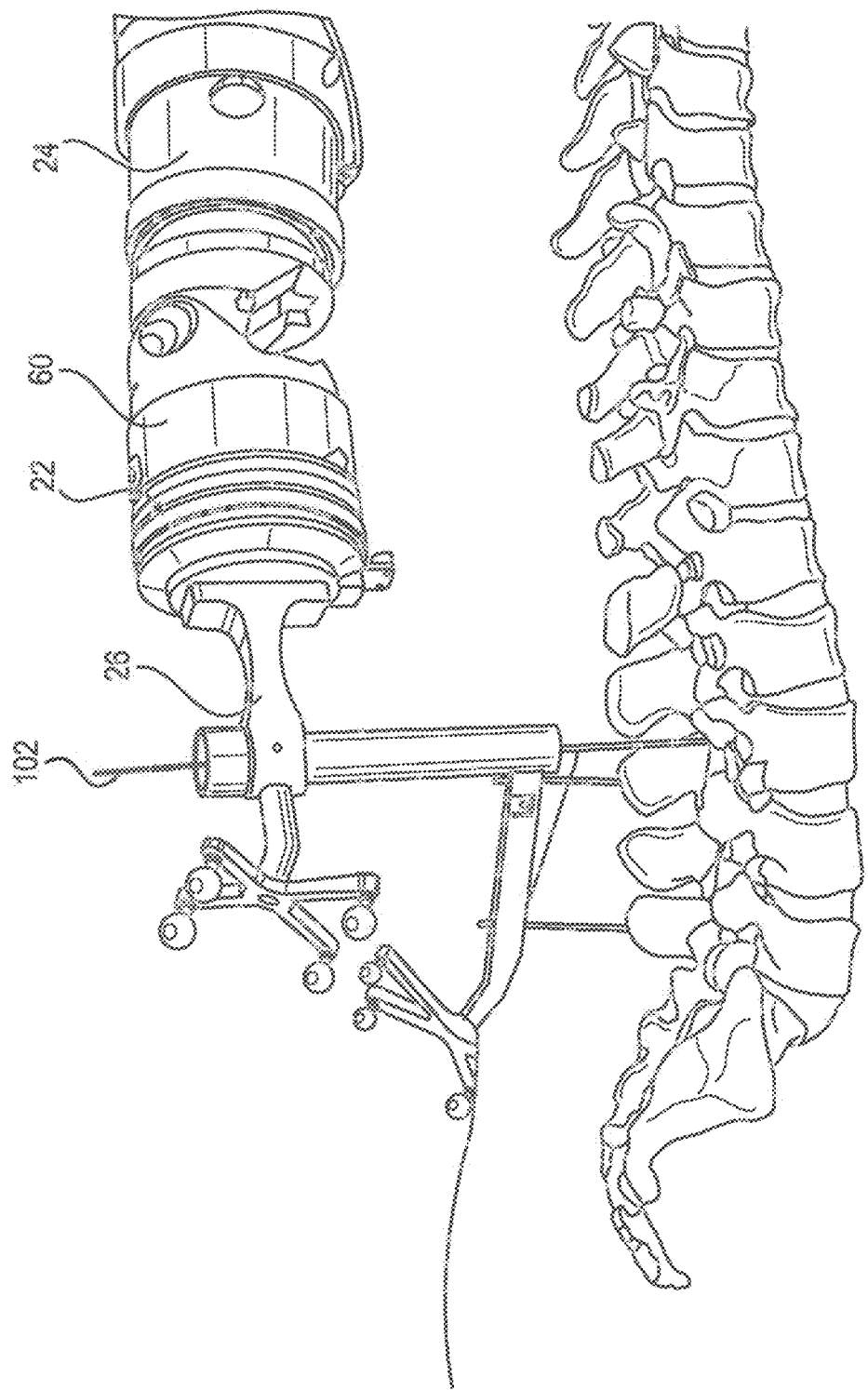
FIG. 14 illustrates an embodiment of an end effector tool positioned along a gravity well.

As illustrated in FIG. 13, a gravity well 102 indicates, in a virtual space, the angle and location end effector tool 26 may need to be positioned for a medical procedure. End effector tool 26, as illustrated, may be moved by an operator using activation assembly 60, discussed above. As end effector tool 26 moves within the area of gravity well 102, the operator may feel the motors in SCARA 24 being to move end effector tool 26 into the programmed position of gravity well 102. As illustrated in FIG. 14, gravity well 102 may maneuver end effector tool 26 into the programmed position. In an example, if the operator begins to move end effector tool 26 using activation assembly 60, the operator may feel the motors provide resistance against the movement. The resistance from the motors may not be strong enough resistance to keep end effector tool 26 within gravity well 102. This may be beneficial as it may allow the operator to maneuver end effector tool 26 to additional gravity wells 102. Gravity well 102 may be programmed into automated medical system 2 before the medical operation and/or during the medical operation. This may allow medical personnel to move a gravity well 102 based on the changing conditions of the medical procedure. Gravity wells 102 may allow automated medical system 2 to place end effector tools 26 in the required area quickly, easily, and correctly.

Figure 15:
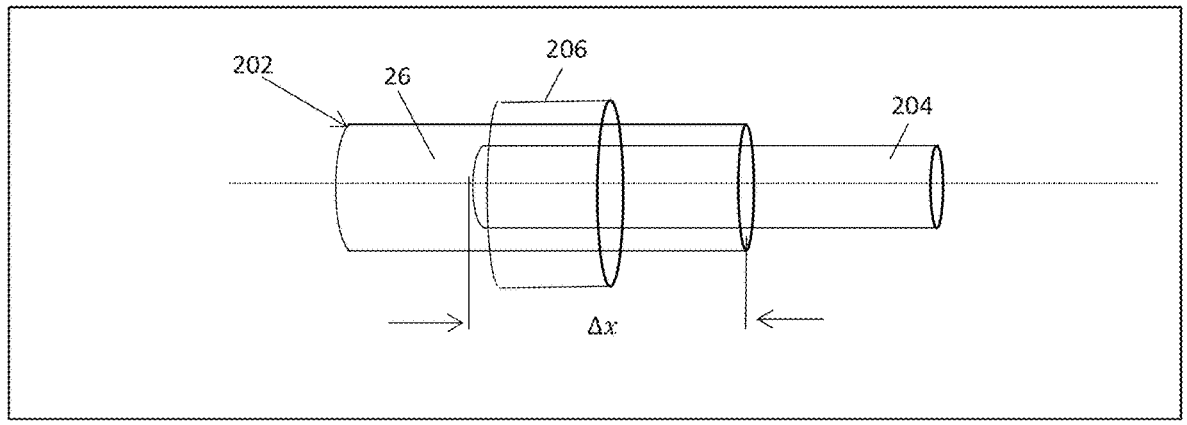
FIG. 15 illustrates a portion of the end effector tool having a hollow tube and positioning of a coil in a metal detector according to one aspect of the present invention.

FIG. 15 illustrates a portion of the robot's end effector 22 including the tool portion 26 defining hollow tube 202. In a robot-assisted surgery, a metal object, such as a metallic surgical instrument 204, is inserted into the hollow tube 202. The hollow tube 202 is sized and configured to receive at least a portion of the metallic surgical instrument 204. The metal object may include any suitable surgical instrument 204 known in the art including, but not limited to, a guide wire, a cannula, a retractor, a drill, a reamer, a driver, an insertion tool, a removal tool, or the like. Although the hollow tube 202 is generally shown as having a cylindrical configuration, it will be appreciated by those of skill in the art that the hollow tube 202 may have any suitable shape, size and configuration desired to accommodate the surgical instrument 204 and access the surgical site.

Before the surgical procedure takes place, the hollow tube 202 is configured to be aligned and/or oriented by the robot arm 20 such that insertion and/or trajectory for the surgical instrument 204 is able to reach a desired anatomical target within or upon the body of the patient. Thus, the surgical instrument 204 may be inserted into the hollow tube 202 after operating the robot 4 to achieve this desired alignment and/or orientation for the desired surgical procedure. Preferably, the robotic system is shut down once the metal surgical instrument 204 is inserted through a portion of the hollow tube 202 or through the entire hollow tube 202. Thus, when the metallic surgical instrument 204 is inserted into the tube 202, the presence of the instrument 204 and/or insertion of the instrument 204 should be detected in order to shut off one or more electronic components of the robot 4, such as cameras, infrared detectors, or the like for safety reasons. This safety mechanism ensures that the robot 4, in particular, the robot arm 20, and more particularly, end effector 22, does not move when the metallic surgical instrument 204 is present in the end effector 22. Thus, this automatic shut off system ensures the safety of the patient because the trajectory and orientation of the surgical instrument 204 positioned through tube 202 cannot change during the operation.

In order to detect the presence of a metallic surgical instrument 204 within the tube 202, a sensor may be used. For example, the sensor may be in the form of an inductor coil 206. As shown in FIG. 15, an inductor coil 206 is positioned around the hollow tube 204. The inductor coil 206 may be positioned either inside or outside of the tube 204. In addition, the inductor coil 206 may be positioned at a suitable location along the length of the tube 202. For example, the coil 206 may be positioned substantially at the longitudinal center of the tube 202. It may be appreciated that the coil 206 may be positioned at another location along the length of the tube 202, e.g., proximate the distal or proximal end.

Figure 16:
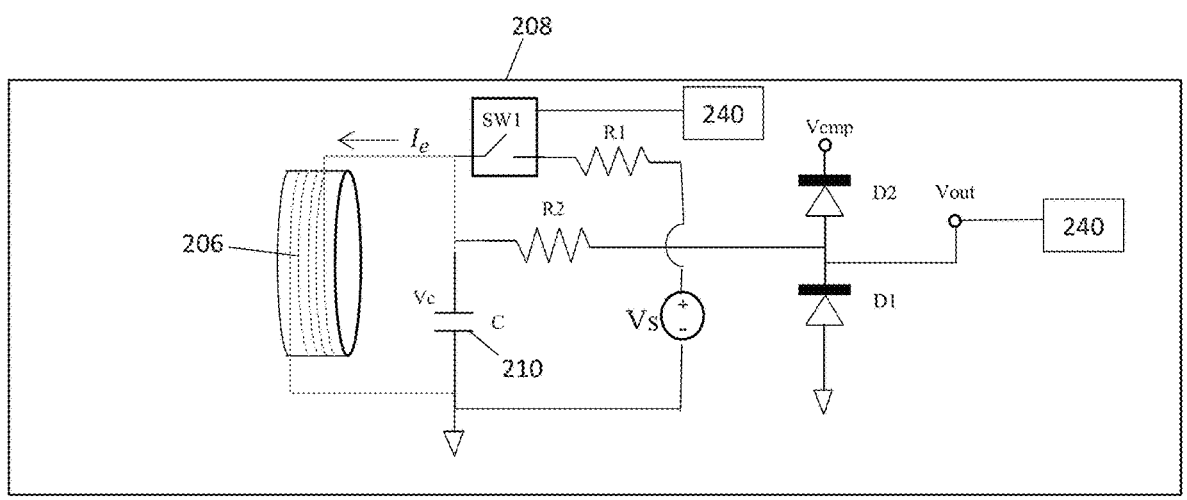
FIG. 16 is a schematic diagram of a waveform generator according to an aspect of the present invention.

FIG. 16 is a schematic diagram of a decaying waveform generator 208 according to an aspect of the present invention. A capacitor 210 connected in parallel with the inductor 206 define a resonance circuit of the generator 208. A voltage source Vs provides current to the resonance circuit through a current limiting resistor R1 which is connected in series with a switch SW1. A second resistor R2 is connected between the resonant circuit and an output terminal Vout.

A first clamp diode D1 has an anode connected to ground and a cathode connected to the output terminal Vout. A second clamp diode D2 has an anode connected to the output terminal Vout and a cathode connected to a reference voltage source Vcmp. The switch SW1 is under the control of a controller 240 as shown in FIG. 17.

Briefly, in operation, when the controller 240 turns on the switch SW1 for a predetermined time period τ, the switch SW1 connects the voltage source Vs to the resonant circuit (206, 210) to allow current from the voltage source Vs to flow into the coil 206 and place an initial voltage Vc across the capacitor 210. This action also sets the initial charge in the inductor L to a value (Vs·τ), where τ is the switch on time.

When the controller 240 turns off the switch SW1, the voltage source Vs is disconnected from the resonant circuit (206, 210) and the voltage across the capacitor 210 starts to oscillate in a decaying manner. The resistor R2 sets the current being provided to the output terminal Vo. The clamping diode D1 ensures that the voltage at the output terminal Vout does not fall substantially below ground. If the capacitor 210 tries to pull the output voltage below zero, the diode D1 turns on and forces the output terminal Vout to ground voltage less the forward biasing voltage (e.g., 0.3 V) of the diode such that the minimum voltage at the output terminal Vout is −0.3 Volt. In effect, the clamping diode D1 acts as a rectifier to provide only a positive voltage to the output terminal Vout.

If, on the other hand, the voltage at the output terminal Vout tries to go above the reference voltage Vcmp, the clamping diode D2 turns on and clamps the output voltage to Vcmp plus the forward biasing voltage (e.g., 0.3 V) of the diode. The reference voltage Vcmp can be set to the maximum voltage permissible (e.g., 5 V) for the controller 240 to make the waveform generator 208 suitable for any number of microcontroller units on the market. Thus, the maximum voltage at the output terminal Vout is 5.3 Volt.

In case the controller 240 fails to turn off the switch SW1, e.g., the controller 240 becomes frozen, the current limiting resistor R1 (e.g., 330 Ohms) ensures that the coil 206 does not become damaged.

Immediately after the switch SW1 is turned off, the resulting decaying waveform at the output terminal Vout is stored in the controller 240. The stored decaying waveform can then be analyzed to determine the effective Q-value of the resonant circuit. In the present configuration, the Q value of the circuit is $$= \frac{\sqrt{L/C}}{ESR},$$

where ESR is the coils "Effective Series Resistance". The Q value can change depending on both the inductance of the coil, and its ESR, and it is this change in Q that is responsible for the change in decay of the waveform. The effective Q value can be used to determine the presence of a metal object 204 inside the hollow tube 202 and the depth of insertion to determine, for example, whether the metal object has been fully inserted as will be explained in more detail below.

FIG. 17 is a schematic diagram of a controller 240 for detecting the presence of or insertion of a metal object 204 in tube 202 according to an aspect of the present invention.

The controller 240 of the present invention is connected to the output terminal Vout and switch SW1 through a communication link 252 which is connected to an I/O interface 242, which receives information from and sends information over the communication link 252. The controller 240 includes memory storage 244 such as RAM (random access memory), processor (CPU) 246, program storage 248 such as FPGA, ROM or EEPROM, and data storage 250 such as a hard disk, all commonly connected to each other through a bus 253. The program storage 248 stores, among others, metal detection module 254 containing software to be executed by the processor 246.

The metal detection module 254 executed by the processor 246 controls the switch SW1. The module 254 can also control the inductor 206 and capacitor 210 if variable inductor or capacitor were used in order to control the frequency of the decaying waveform.

The metal detection module 254 includes a user interface module that interacts with the user through the display device 211 and input devices such as keyboard 212 and pointing device 214 such as arrow keys, mouse or track ball. The user interface module assists the user in programming the programmable components in the waveform generator 208 and calibration of data as will be explained in more detail herein. Any of the software program modules in the program storage 248 and data from the data storage 250 can be transferred to the memory 244 as needed and is executed by the CPU 246.

An analog-to-digital (A/D) converter 243 is connected to the I/O interface 242. The A/D converter 243 converts the analog decaying waveform at the output terminal Vout into digital data to be stored in the storage 250 by the processor 246.

One exemplary controller 240 may be 8051 microcontroller from Intel Corporation of Santa Clara, CA However, any processor or microcontroller that offers an A/D converter can be used.

In one embodiment, parts of or the entire the controller 240 including the input devices 212, 214 and display device 211 can be incorporated into the automated medical system 2 of FIG. 1. For example, the display 211 can be the same as display 34.

Figure 21:
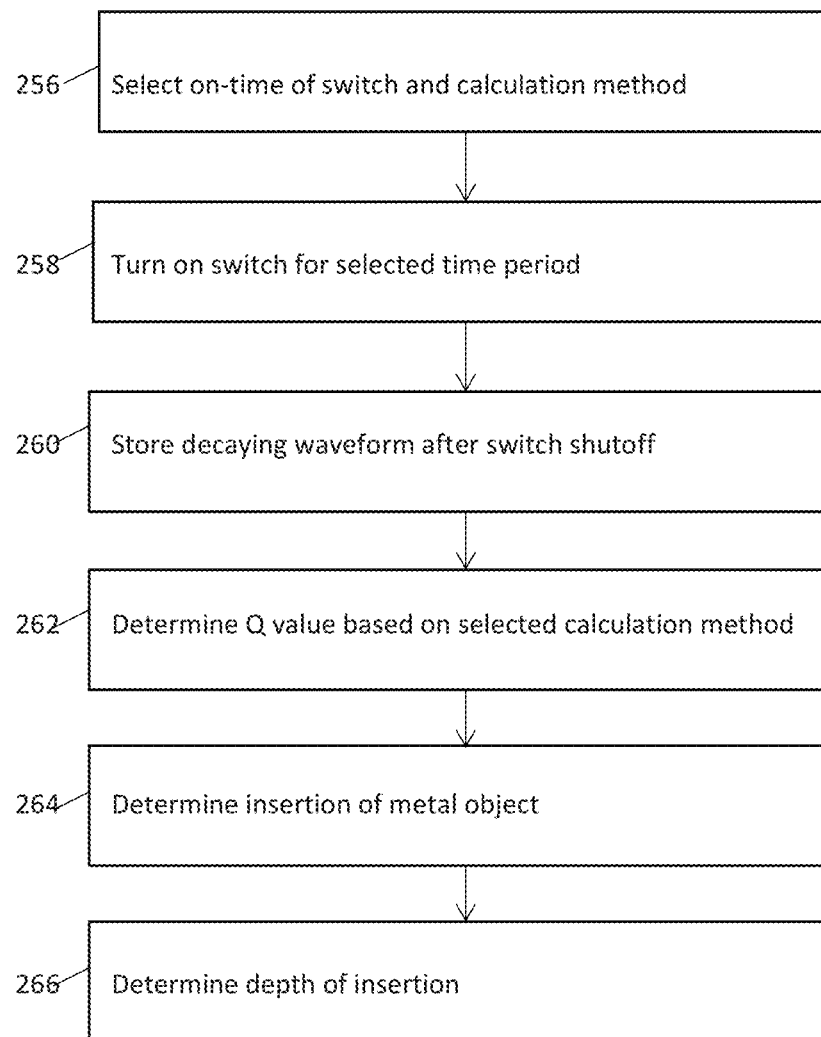
FIG. 21 is a flowchart of a method of performing metal detection and depth determination according to one aspect of the present invention.

A method of performing metal detection and/or depth determination (e.g., of surgical instrument 204) by the metal detection module 254 will now be explained with reference to FIG. 21. In step 256, the user interface of the metal detection module 254 interacts with the user in selecting the switch-on time τ, metal detection calculation method, and calibration mode, which are stored in the data storage 250. If the user or the module 254 itself selects the calibration mode, then all of the steps are used to determine an initial Q value (and initial inductance value) without any metal object for storage in the storage 250 for later use in determining the presence and depth of the metal object 204 inside the hollow tube 202.

In step 258, the controller 240 sends a signal through the link 252 to turn on the switch SW1 for a preselected time (e.g., 100 microseconds). The switch SW1 connects the voltage source Vs to the resonant circuit (6,10) and current $I_e$ flows through R1. This places an initial voltage Vs across the capacitor 210, and pre-charges the coil 206 to an initial flux level of (Vs·τ). This magnetic charge is then built up in the coil 206 until the switch SW1 turns off. Once the switch SW1 turns off, the resonating current in the resonant circuit outputs a decaying waveform.

In step 260, the decaying waveform at the output terminal Vout is converted into digital data and stored in the storage 250.

In step 262, a Q value of the inductor 206 is calculated by the following methods.

The initial current in the coil 206 may be set by two different methods. The first method is by keeping the switch SW1 closed for a sufficiently long time, allowing $I_e$ to settle to $$\frac{v}{(R1 + ESR)}.$$

The other method is to keep the switch SW1 on for a "short time" τ setting the initial current to $$\frac{v}{L} \cdot \tau,$$

where L is the inductance of the coil 206.

After such initial current is established in the coil 206 and initial voltage across the capacitor 210, SW1 opens and the circuit is allowed to resonate at its own natural frequency as a decaying voltage waveform at the capacitor 210. The voltage across the capacitor 210 may be monitored to calculate what the Q value of the coil 206 is. The relationship between the time domain voltage across the capacitor ($V_c(t)$) and the coil's inductance L is realized in equation 1:

$$V_c(t) = \frac{v \cdot \omega_0^2 \cdot e^{-\gamma \cdot t}}{\gamma^2 + \omega_n^2} \cdot \left[ (\gamma - \tau \cdot \gamma^2 - \tau \cdot \omega_n^2) \cdot \sin(\omega_n \cdot t) + \omega_n \cdot \cos(\omega_n \cdot t) \right] - \qquad (1)$$

$$v \cdot \frac{\omega_0^2 - \gamma^2 - \omega_n^2}{\gamma^2 + \omega_n^2}$$

Where:

$$\gamma = \frac{1}{2} \cdot \frac{R_{ESR}}{L},$$

$$\omega_0 = \frac{1}{\sqrt{L \cdot C}},$$

$$\omega_n = \sqrt{\omega_0^2 - \gamma^2}$$

v=source voltage Vs, $\omega_0$=natural undamped resonant frequency of coil 206 and capacitor 210, γ=damping coefficient of coil 206 and capacitor 210, which includes the ESR (Effective Series Resistance) of the coil, τ=on time of the switch SW1, and $\omega_n$=natural resonant frequency.

Note that γ defined above contains both the ESR and the coil's inductance L, and is therefore directly related to the Q value. The relationship is:

$$Q = \frac{1}{\omega_0} \cdot \frac{1}{2 \cdot \gamma} \quad (2)$$

Figure 18:
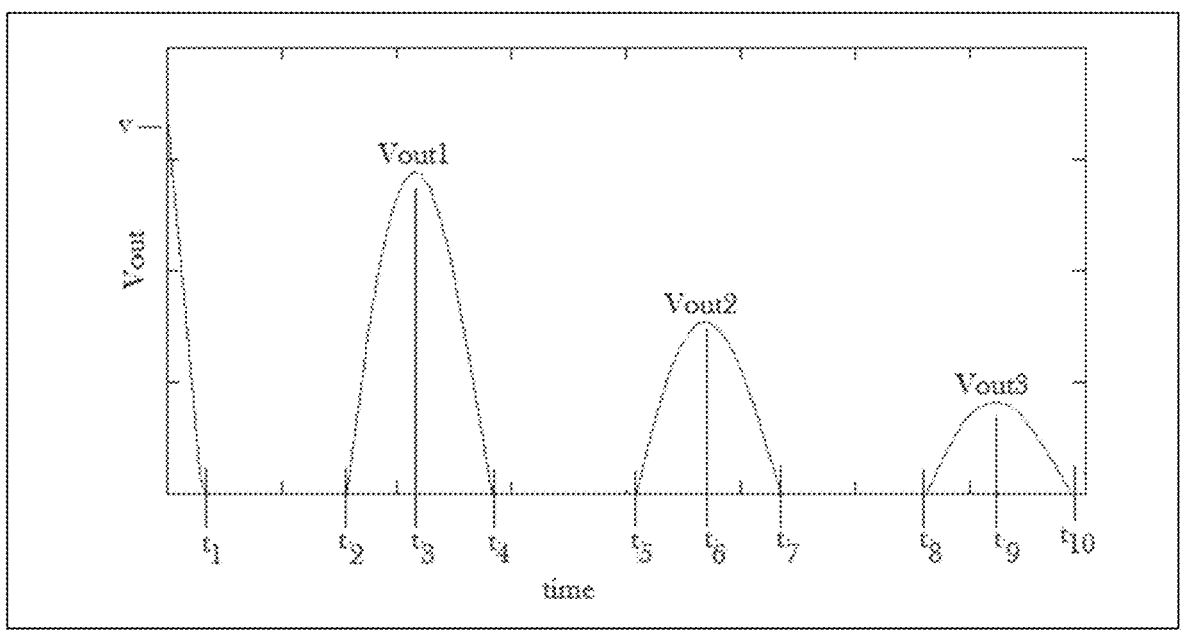
FIG. 18 is an exemplary decaying waveform of the waveform generator.

The voltage across the capacitor 210 produces a current in R2 and a typical waveform produced at the output terminal Vout is shown in FIG. 18. At t=0, the switch SW1 shuts off. As shown in FIG. 18, only the first three waves (t2 to t4, t5 to t7 and t8 to t10) in the waveform are shown. The waveform has a first peak voltage at t=t3, second peak at t=t6 and third peak at t=t9.

The decaying waveform may be used in many ways to calculate what the Q value of the coil 206 is. A first method to determine the Q value is to measure the "average value" of the waveform. An average value can be realized by calculating the integral of the area under the waveform over a predetermined number of waves or time period and then dividing by the time interval where the voltage is present. A relationship between the average value and Q value can be determined empirically or by equation (1).

Another way to determine the Q value is to measure one or more of the peak voltages Vout1, Vout2 and Vout3 and their corresponding times t3, t6 and t9. For example, the voltage value at the first peak (i.e., Vout1 in FIG. 17) and t=t3 can be determined. From these values, the Q value may be computed from equation (1).

Another way to determine the Q value is to measure the zero crossing voltages that occur at times t2, t4, t5, t7, t8 and t10. From these values, the Q value may be computed from equation (1).

Yet another way to determine the Q value is to measure the signal energy of the waveform over a time "window" by computing the integral of the waveform in the time $t_0$-$t_n$, such that $t_n > 3\tau$ where $\tau$ is the time constant of the resonant circuit. From these values, the Q value may be computed from equation (1).

Among those described above, one exemplary embodiment uses the fourth method of integrating over a time window. As the waveform signal is sampled by the A/D converter 243 over some time t, the metal detection module 254 of the controller 240 can compute a sum of the sampled signals as a way to integrate the signal. That sum can be compared or characterized to different values of Q by equation (1) above or empirically. The characterization can be stored in storage as a lookup table which can then be retrieved and used by the metal detection module 254 with interpolation.

In step 264, the metal detection module 254 determines whether the metal object 204 is present in the hollow tube 202. As an example, in one embodiment, assume that the user has selected the first peak voltage determination as the method of obtaining a Q value in step 256. Once the Q value has been obtained from the first peak voltage and t3 values, the metal detection module 254 compares it to a threshold value which has been preselected.

Figure 20:
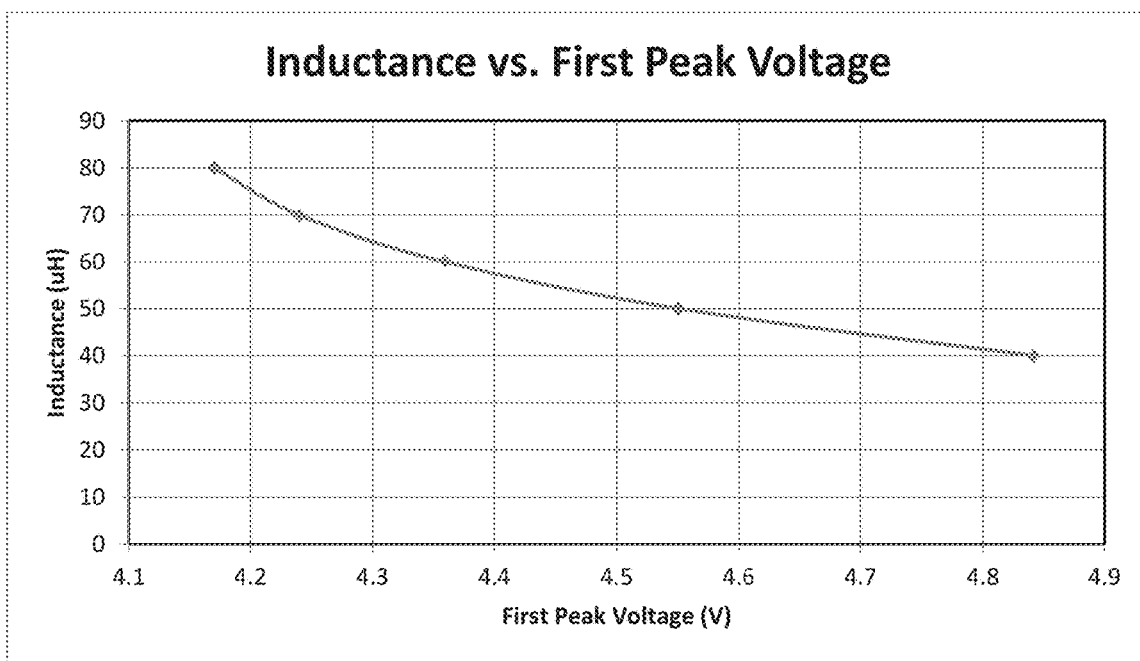
FIG. 20 is a graph of inductance values as a function of the first peak voltage of several decaying waveforms.

In some cases, the ESR doesn't change much. If this is the case, the Q value is purely a function of the inductance only. FIG. 20 shows a graph of the computed inductance values vs. the voltage values at the first peak value (i.e., Vout1 at t=t3 in FIG. 17) once the initial voltage at t=0 falls to ground. Based on the graph, the threshold inductance value can be set at 50 µH below which the metal detection module 254 considers the metal object to be present (e.g., metal object is substantially fully inserted into the tube 202). Alternatively, the graph of FIG. 20 can be converted to a graph of Q values vs. first peak voltage and a Q-value threshold value equivalent to L=50 µH can be stored as the threshold Q value.

Another way to detect the presence is to empirically obtain a threshold Q value (or inductance value) under which the module 254 determines that the metal object 204 is present in the hollow tube 202. This can be done by inserting the metal object 204 into the hollow tube 202 at a user-selected depth and determining the Q value (or inductance value) based on a decaying waveform.

In step 266, the metal detection module 254 determines how deep the metal object 204 is inside the hollow tube 202. One way to determine the depth is to empirically obtain a lookup table of Q values (or inductance values) at various depths for a given metal object 204.

Figure 19:
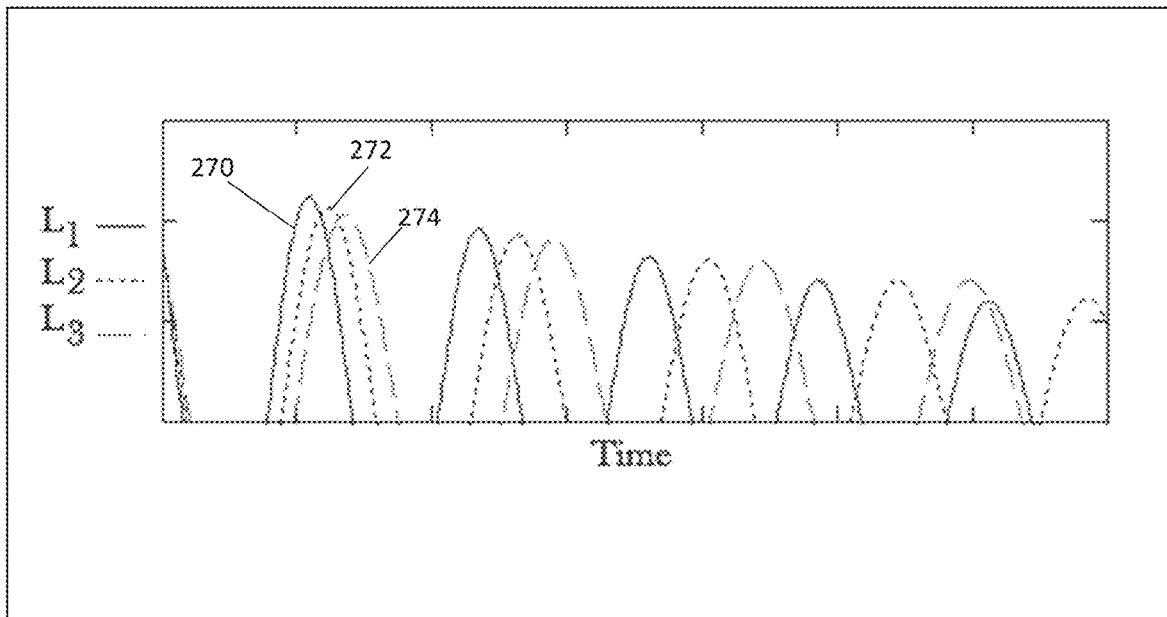
FIG. 19 illustrates several decaying waveforms from the waveform generator which may represent the depth of insertion of the metal object into the hollow tube.

FIG. 19 illustrates several decaying waveforms from the waveform generator 208 which represent the depth of insertion of the metal object 204 into the hollow tube 202. Waveform 270 represents one in which no metal object is present. Waveform 270 equates to the original Q value of Q1 without any metal object insertion. Waveform 272 represent one in which the metal object 204 has been inserted half way, i.e., the distal end of the metal object 204 is at a midpoint between the center of the tube 202 and proximal end of the tube. Waveform 72 equates to Q value of Q2 which is less than Q1. Waveform 274 represent one in which the metal object 204 has been inserted fully, i.e., the distal end of the metal object 204 is at the center of the coil 206. Waveform 274 equates to Q value of Q3 which is less than Q2. Thus, the insertion depth of the metal object 204 is negatively correlated to the Q value.

Based on such empirical data, a lookup table can be prepared. The table equates various Q values to respective distance Δx (i.e., depth). Once the table is obtained, it is stored in the storage 250 and is used by the metal detection module 254 to obtain the depth of insertion of the metal object 204 based on the Q value from step 262.

Figure 22:
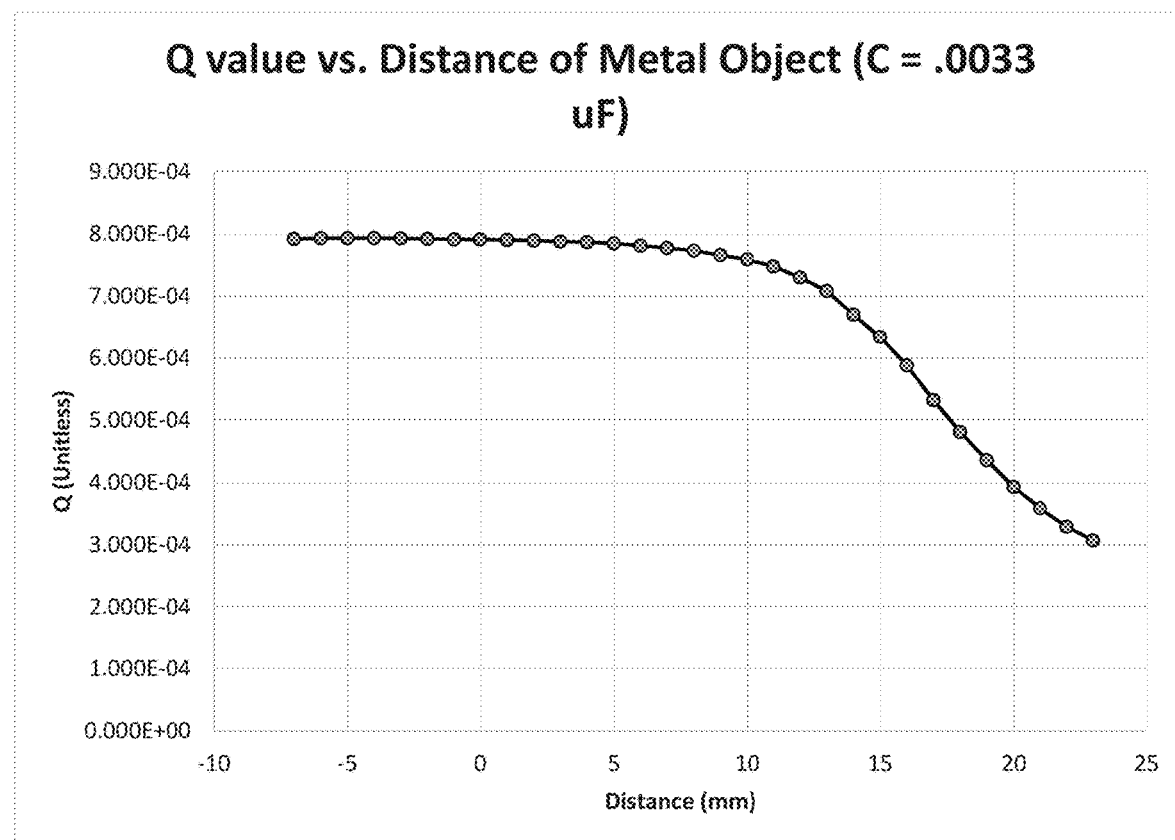
FIG. 22 is a graph of Q values as a function of the depth of insertion of the metal object into the hollow tube.

Another example of a lookup table is shown in FIG. 22. FIG. 22 shows a graph of Q values as a function of the depth of insertion of the metal object into the hollow tube (distance Δx). The experiment was performed with a 6 mm diameter Ferrite metal object (cylinder) and a 15 mm diameter by 8 mm length coil. The distance Δx represents the distance from the distal end of the metal cylinder and the center of the coil. As can be seen, as the metal cylinder 204 is inserted into the hollow tube 202, the Q value changes. The graph of FIG. 22 can be stored in the storage 250 as a lookup table for retrieval by the metal detection module 254. Interpolation may need to be used if the lookup table is stored as a set of discrete points, rather than an equation.

In step 266, the metal detection module 254 looks up the depth value from the lookup table stored in the storage 250 for a given Q value which was found in step 262. The depth value from the lookup table is generated as the output from the metal detection module 254.

In the embodiment shown, a rectified decaying waveform has been used because it is relatively simple to integrate over the waveform. If a full non-rectified decaying waveform is used, more components will be needed as a simple method of integrating will not work because of the symmetry of the waves.

Although the present invention has been described above with the coil which is positioned at the center of the tube 202, it is possible to position the coil at the proximal end, distal end or anywhere along the tube. It is also possible to use multiple coils that are spaced apart. For example, three coils (respectively positioned at the proximal end, center and distal end) that are uniformly spaced from each other can be used to detect the presence and depth of the metal object inside the hollow tube 202. As can be appreciated, this embodiment can be particularly useful when determining the depth of the metal object (e.g., surgical instrument 204) in the hollow tube 202. If multiple coils are used, it is preferable to separate the on time of the switch SW1 for each inductor coil (e.g., turning on and off the resonant circuit and measuring the inductance value prior to turning on the next resonant circuit) so as to prevent one resonant circuit from interfering with another.

Advantageously, the present invention uses minimum number of components by utilizing the power of a processor such as a microcontroller for the processing of waveforms. The circuit in the form of a waveform generator 208 requires only the switch SW1, capacitor 210 and inductor 206.

Accordingly, before the surgical procedure takes place, the hollow tube 202 is aligned and/or oriented by the robot 4 in order to obtain a desired insertion angle and/or trajectory for the surgical instrument 204. After properly positioned, the surgical instrument 204 may be inserted into the hollow tube 202. In order to ensure the desired alignment, the robotic system is shut down by the presence of the surgical instrument 204 in the tube 202 or at a certain depth therein. Thus, when the surgical instrument 204 is inserted into the tube 202, the mere presence of the instrument 204 triggers an automatic shut off of certain robotic components (e.g., those the control or allow for movement of the robotic arm 20. This automatic shut off ensures the trajectory and orientation of the surgical instrument 204, and thus cannot change during the operation. In order to move, the robot arm 20, the instrument 204 must be removed from the tube 202, thereby ensuring safety of the patient.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. An automated medical system comprising:
a robot body;
a robot arm configured to be supported by the robot body; and
an end effector removably attachable to the robot arm, the end effector including a hollow tube and a metal detector for detecting insertion of a metallic surgical device into the hollow tube, wherein the metal detector further includes:
a controller connected to a switch and a resonant circuit, and operable to turn on the switch for a preselected time period to temporarily provide a current to the resonant circuit and analyze a decaying voltage waveform originating from the resonant circuit when the switch is turned off to determine a presence of the metallic surgical device in the hollow tube.

2. The system of claim 1, wherein the metal detector further includes a first clamp diode having an anode connected to ground and a cathode connected to an output terminal to prevent the voltage at the capacitor from falling below ground.

3. The system of claim 1, wherein the metal detector further includes a second clamp diode having an anode connected to an output terminal and a cathode connected to a reference voltage source to prevent the voltage at the capacitor from rising past the reference voltage.

4. The system of claim 1, wherein the controller detects the presence of the metallic surgical device inside the hollow tube by determining a Q value from the decaying voltage waveform.

5. The system claim 1, wherein the controller determines the presence of the metallic surgical device by determining an average value of the waveform.

6. The system of claim 1, wherein the controller determines the presence of the metallic surgical device by determining the peak value of at least one of the waves in the decaying waveform.

7. The system of claim 1, wherein the controller determines the presence of the metallic surgical device by determining times at which the waves in the decaying waveform cross a preselected voltage value.

8. The system of claim 1, wherein the controller determines the presence of the metallic surgical device by determining a signal energy of the decaying waveform over a preselected time window.

9. The system of claim 8, wherein the controller determines the presence of the metallic surgical device by determining an integral of the decaying waveform over the preselected time window.

10. The system of claim 1, wherein the controller determines a longitudinal position of the metallic surgical device inside the hollow tube from the decaying waveform.

11. An automated medical system comprising:
a robot body;
a robot arm configured to be supported by the robot body;
an end effector removably attachable to the robot arm, the end effector including a hollow tube and a metal detector for detecting insertion of a metallic surgical device into a hollow tube;
a camera configured to track the end effector;
wherein the metal detector further includes:
a controller connected to a switch and a resonant circuit, and operable to turn on the switch for a preselected time period to temporarily provide a current to the resonant circuit and analyze a decaying voltage waveform originating from the resonant circuit when the switch is turned off to determine a presence of the metallic surgical device in the hollow tube.

12. The system of claim 11, wherein the metal detector further includes a first clamp diode having an anode connected to ground and a cathode connected to an output terminal to prevent the voltage at the capacitor from falling below ground.

13. The system of claim 11, wherein the metal detector further includes a second clamp diode having an anode connected to an output terminal and a cathode connected to a reference voltage source to prevent the voltage at the capacitor from rising past the reference voltage.

14. The system of claim 11, wherein the controller detects the presence of the metallic surgical device inside the hollow tube by determining a Q value from the decaying voltage waveform.

15. The system claim 11, wherein the controller determines the presence of the metallic surgical device by determining an average value of the waveform.

16. The system of claim 11, wherein the controller determines the presence of the metallic surgical device by determining the peak value of at least one of the waves in the decaying waveform.

17. The system of claim 11, wherein the controller determines the presence of the metallic surgical device by determining times at which the waves in the decaying waveform cross a preselected voltage value.

18. The system of claim 11, wherein the controller determines the presence of the metallic surgical device by determining a signal energy of the decaying waveform over a preselected time window.

19. The system of claim 18, wherein the controller determines the presence of the metallic surgical device by determining an integral of the decaying waveform over the preselected time window.

20. The system of claim 11, wherein the controller determines a longitudinal position of the metallic surgical device inside the hollow tube from the decaying waveform.

* * * * *